(12) United States Patent
Kao et al.

(10) Patent No.: US 6,310,083 B1
(45) Date of Patent: Oct. 30, 2001

(54) CAGED AMINO ACID DERIVATIVES BEARING PHOTOLABILE PROTECTIVE GROUPS

(75) Inventors: Joseph P.Y. Kao, Silver Spring, MD (US); Francis M. Rossi, Mountain View, CA (US)

(73) Assignee: University of Maryland Boitechnology Institute, Baltimore, MD (US)

( * ) Notice: Subject to any disclaimer, the term of this patent is extended or adjusted under 35 U.S.C. 154(b) by 0 days.

(21) Appl. No.: 09/216,858

(22) Filed: Dec. 21, 1998

(51) Int. Cl.[7] .................... A61K 31/415; A61K 31/405; A61K 31/195
(52) U.S. Cl. .................. 514/396; 514/415; 514/426; 514/561; 514/562; 514/563; 514/564; 514/565; 514/566; 514/567
(58) Field of Search ................. 548/339.1, 496, 548/535; 560/20, 21, 22, 23; 514/396, 415, 426, 561–567

(56) References Cited

U.S. PATENT DOCUMENTS 5,430,175   7/1995   Hess .

OTHER PUBLICATIONS

Rossi, F M, et al. "Nmoc–DBHQ, a new caged molecule for modulating sarsoplasmic/endoplasmic reticulum Ca ATPase activity with light flashers" J. Biol. Chem., vol. 272, No. 6, pp. 3266–3271, Feb. 1997.*

Pillai, V N R, "Photoremovable protecting groups in organic synthesis" Synthesis, pp. 1–26, 1980.*

Corrie, J E T et al. "Postsynaptic activation at the squid giant synapse by photolytic releas of L–glutamate from a caged'L–glutamate" J. Physiol. (London) vol. 465, pp. 1–8, 1993.*

Wiebodlt, R, et al. "Photolabile precursors of glutamate- :Synthesis, photochemical properties, and activation of glutamate receprors on a microsecond time scale" Proc. Natl. Acad. Sci. USA, vol. 91, pp. 8752–8756, 1994.*

Hasan, A, et al. "Photolabile protecting groups for nucleosides: Synthesis and photodeprotection rates" Tetrahedron, vol. 53, No. 12, pp. 4247–4264, 1997.*

Amit, B, et al. "Photosensitive protection groups of amino sugars and their use in glycoside synthesis. Nitrobenzyloxyamino and 6–nitrovaleratryloxycarbonylamino derivatives" J. Org. Chem. vol. 39, No. 2, pp. 192–196, 1974.*

Burgess, K, et al. "An approach to photolabile, fluorescent protecting groups" J. Org. Chem. vol. 62, pp. 5165–5168, 1997.*

Rossi et al, J. Biol. Chem., 272(52):32933–32939 (1997).

Rossi et al, J. Biol Chem., 272(6): 3266–3271 (1997).

Rossi et al, The American Society for Cell Biology, 35th Annual Meeting, Washington, D.C., Abstract No. 2038, p. 351a (Dec. 9–13, 1995).

Rossi et al, American Chemical Society, Division of Organic Chemistry, 211th ACS National Meeting, New Orleans, LA, Abstract No. 192 (Mar. 24–28, 1996).

Muralidharan et al, J. of Photochem. Photobiol., 27: 123–137 (1995).

Haugland, "Handbook of Fluorescent Probes and Research Chemicals", 6th Ed., (Molecular Probes, Inc.: Eugene (OR)), pp. 447–455 (Nov. 16, 1996).

Kao et al, J. Biol. Chem., 264(14): 8179–8184 (1989).

Kao et al, Meth. Cell. Biol., 40: 155–181 (1994).

Berven et al, FEBS Letter, 346: 235–240 (1994).

Kao et al, FASEB J., 9(3): A392 (1995).

* cited by examiner

Primary Examiner—Gary Geist
Assistant Examiner—Leigh C. Maier
(74) Attorney, Agent, or Firm—Sughrue, Mion, Zinn, Macpeak & Seas, PLLC

(57) ABSTRACT

Derivatives of o-nitromandelyoxycarbonyl (Nmoc) which are capable of releasing an amino acid (or derivative thereof), upon irradiation with ultraviolet (UV) light are disclosed, as well as a method for producing a free amino acid (or derivative thereof) employing the same, e.g., to study neurophysiology.

14 Claims, 15 Drawing Sheets

FIGURE 11
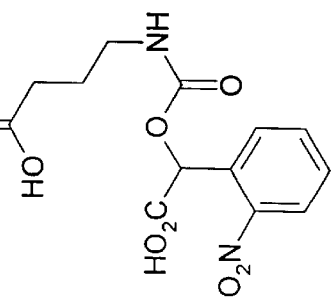
10
N-Nmoc-γ-aminobutyric acid
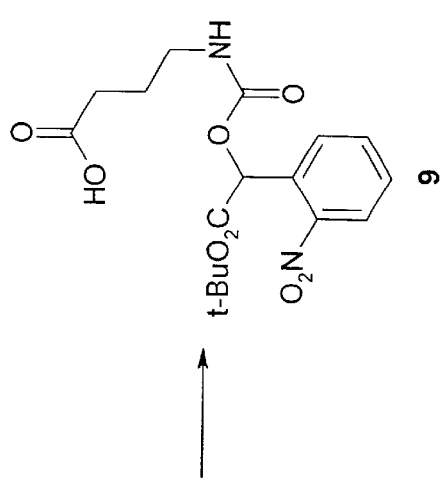
9
N-(t-Butyl-Nmoc)-γ-aminobutyric acid
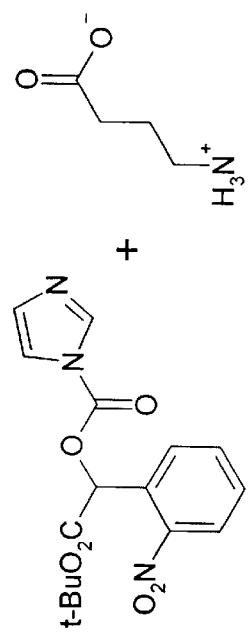
γ-Aminobutyric acid
4

CAGED AMINO ACID DERIVATIVES BEARING PHOTOLABILE PROTECTIVE GROUPS

FIELD OF THE INVENTION

The present invention relates to derivatives of o-nitromandelyoxycarbonyl (Nmoc) which are capable of releasing amino acids (or derivatives thereof), upon irradiation with ultraviolet (UV) light, and a method for producing amino acids (or derivatives thereof) employing the same, e.g., to study neurophysiology.

BACKGROUND OF THE INVENTION

Non-N-methyl-D-aspartate (NMDA) glutamate receptor (GluR) channels are the molecular entities that mediate the majority of the fast excitatory synaptic transmissions in the mammalian central nervous system (Mayer et al, *J. Physiol.*, 354:29–53 (1984)). Studies aimed at improving understanding of the properties of synaptic non-NMDA GluR channels by direct application of glutamate is severely limited by poor access in the intact preparation. A potential solution to this problem is the use of "caged" compounds.

A caged compound is an effector molecule whose activity is temporarily masked by the attachment of a photosensitive masking, or caging, group (Kao et al, *In: Optical Microscopy: Emerging Methods and Applications*, Herman et al, Eds., Academic Press, San Diego, pages 27–85 (1993); and Adams et al, *Ann. Rev. Physiol.*, 55:755–784 (1993)). Cleavage of the caging group by flash photolysis rapidly liberates the fully bioactive molecule to cause a "jump" in the concentration of the effector molecule. This feature, coupled with the fact that photolysis can be achieved with highly focused light beams, means that photorelease of caged molecules can afford excellent spatial and temporal control over reagent delivery to biological preparations.

In situ photorelease of caged glutamate offers a potentially powerful means for studying the properties of synaptic GluR's, their distribution, and for eliciting action potentials from afar in a specifically targeted neuron (Wang et al, *Neuron*, 15:755–760 (1995); and Katz et al, *J. Neurosci. Meth.*, 54:205–218 (1994)). However, a number of distinctive properties of GluRs present formidable challenges to the design of caged glutamate reagents. The non-NMDA subset of GluRs require>1.0 mM glutamate for full activation, yet<10 µM glutamate can induce significant desensitization in these same GluRs (Trussell et al, *Neuron*, 3:209–218 (1989); and Tang et al, *Science*, 243:1474–1477 (1989)). Furthermore, 10 µM glutamate is sufficient to activate the NMDA subset of GluRs (Mayer et al, supra). An ideal caged glutamate should, therefore, give high yield of free glutamate on photolysis, and should have minimal pre-photolysis activity and high chemical stability. Moreover, because entry into desensitization occurs on the several-millisecond time scale, photorelease must be sufficiently rapid to outpace desensitization. Although there has been considerable effort to perfect a caged glutamate (Wilcox et al, *J. Org. Chem.*, 55:1585–1589 (1990); Corrie et al, *J. Physiol.*, 465:1–8 (1993); Wieboldt et al, *Proc. Natl. Acad. Sci., USA*, 91:8752–8756 (1994a); and Gee et al, *J. Org. Chem.*, 61:1228–1283 (1996)), no caged glutamate to date has fully satisfied all of these criteria. Some show high chemical stability, but very slow photorelease kinetics (Corrie et al, supra), while others uncage rapidly, but either possess significant pre-photolysis activity or are sufficiently labile as to release glutamate slowly even in the absence of light (Wieboldt et al, supra (1994a); and Gee et al, supra (1996)).

More specifically, the currently most useful caged glutamate, γ-O-(α-carboxy-2-nitrobenzyl)-glutamate (γ-CNB-Glu), developed by Hess and colleagues (Wieboldt et al, supra (1994a)), exhibits a photorelease rate and quantum yield that are sufficiently high to suit many biological applications. However, in experiments where a caged glutamate is used at high concentration and/or for extended periods in aqueous solution near neutral pH, significant pre-photolysis bioactivity is evident. The pre-photolysis activity of γ-CNB-Glu, which increases with time near neutral pH, is most likely due to the presence of the benzylic carboxylate in the CNB cage, which can catalyze the spontaneous hydrolysis of the ester linkage between the CNB cage and the γ-carboxyl group of the glutamate side-chain to liberate free glutamate. The "neighboring-group-participation" mechanism (Ritchie, *Physical Organic Chemistry*, Marcel Dekker, New York, pages 80–89 (1975)) for this process is shown in FIG. 1.

As shown in FIG. 1, the benzylic carboxylate first attacks the ester linkage to the γ-carboxyl of glutamate to generate an anhydride. The anhydride is then hydrolyzed by water to yield the intact CNB cage and free glutamate. Such a mechanism involving participation by the neighboring carboxylate on CNB is consistent with the finding herein that generation of pre-photolysis activity increases with time near neutral pH (see FIG. 10B), but is inhibited at rather low pH, because at low pH, the critical carboxylate would become protonated, and thus lose its ability to engage in nucleophilic attack on the ester linkage.

Catalysis by a neighboring carboxylate similarly rationalizes why photorelease of the glutamate γ-carboxyl from the CNB cage is more than 3.5 orders of magnitude faster than from the 1-(2-nitrophenyl)ethyl (NPE) cage, which lacks the benzylic carboxyl group (Wieboldt et al, supra (1994a)) (see FIG. 2).

In designing the compounds of the present invention, retaining the kinetic advantage of the benzylic carboxylate in accelerating photorelease, while eliminating the disadvantage of the same benzylic carboxylate in catalyzing spontaneous hydrolysis of the caged compound to give free glutamate in the absence of light, was sought.

With these concerns in mind, a new caged glutamate has been synthesized and evaluated in the present invention that offers a reasonable compromise in achieving good photolysis yield, rapid kinetics, low intrinsic activity, and chemical stability.

In particular, in N-[2-[2-nitrophenyl]-2-oxycarbonyl acetic acid]-(S)-glutamic acid (N-Nmoc-L-glutamate, or simply, Nmoc-Glu) (FIG. 3), hydrolytic instability is eliminated by attaching the cage to the α-amino group of glutamate through a carbamate linkage, which is quite resistant to hydrolysis (Greene et al, *In: Protective Groups in Organic Synthesis*, Wiley-Interscience, New York, pages 309–405 (1991))). Moreover, retention of the benzylic carboxylate in Nmoc-Glu implies that photochemical cleavage, which is otherwise very slow in carbamate-linked cages (Corrie et al, supra), would be significantly accelerated. It was postulated in the present invention that such a design would dramatically increase the hydrolytic stability of Nmoc-Glu relative to γ-CNB-Glu, with only a modest sacrifice in photorelease quantum yield and speed.

Although vulnerability to spontaneous hydrolysis can largely account for the differences in pre-photolysis activity between Nmoc-Glu and γ-CNB-Glu, there may be other contributing factors. For example, attachment of a caging group may not completely abolish the biological activity of an effector molecule (Kao et al supra; discuss the specific case of caged ATP; see also Nichols et al, Pflügers Arch., 415:510–512 (1990); and Ämmälä et al, *Biochim. Biophys. Acta*, 1092:347–349 (1991)).

The carbamate linkage between the Nmoc group and the α-amino group of glutamate has been found in the present invention to effectively eliminate hydrolytic instability, but at the cost of introducing an additional rate-limiting, pH-dependent decarboxylation step, which slows the final release of free glutamate. Glutamate photorelease from Nmoc-Glu thus occurs on the several-millisecond time scale, which is slower than from γ-CNB-Glu. However, it was found in the present invention that glutamate photorelease is still close to two orders of magnitude faster than from N1-(2-nitrophenyl)ethoxycarbonyl-L-glutamate (NPEOC)-caged glutamate (Corrie et al, supra), which also incorporates a carbamate linkage.

The slower kinetics of glutamate release from Nmoc-Glu can be compensated for in the following two ways:

(1) one can accelerate the rate of glutamate generation by increasing the concentration of Nmoc-Glu.

Because the initial photochemical transformation is extremely fast, the photorelease process shown in FIG. 3 can be approximated as:

where H is the hemiacetal intermediate, C is the carbamate of glutamate, G is free glutamate product, and $k_1$ and $k_2$ are unimolecular rate constants. For such a sequential reaction scheme, the time-course of glutamate release is given by (Moore, *Physical Chemistry*, 4th Ed. Prentice-Hall, Englewood Cliffs, N.J., pages 345–346 (1972)):

$$G(t) = H_0 \left[ 1 + \frac{k_1 e^{-k_2 t} - k_2 e^{-k_1 t}}{k_2 - k_1} \right]$$

where $G(t)$ is the concentration of free glutamate as a function of time, and $H_0$ is the initial concentration of hemiacetal intermediate produced by photolysis. This integrated rate equation shows that the rate of glutamate generation is directly proportional to the concentration of hemiacetal produced initially by photolysis, which is, in turn, directly proportional to the concentration of caged compound used. Therefore, increasing the concentration of caged glutamate will always result in faster accumulation of free glutamate after photolysis. This compensatory approach to increasing the rate of free glutamate photorelease is possible in the case of Nmoc-Glu, because the pre-photolysis activity of Nmoc-Glu is negligible. Thus, increasing the Nmoc-Glu concentration will always lead to faster accumulation of free glutamate without causing unwanted activation or desensitization of GluRs.

(2) because the rate-limiting decarboxylation to release free glutamate is pH-dependent, one can accelerate photorelease by lowering the pH.

The strategy and method developed for caging the amino acid glutamate in the present invention has been found in the present invention to be readily extended and applied to other amino acids and derivatives thereof.

SUMMARY OF THE INVENTION

An object of the present invention is to provide reagents capable of generating amino acids, or derivatives thereof, upon illumination with UV light.

Another object of the present invention is to provide biologically inert compounds which can be taken up by living tissues, and will remain stable inside of living tissues until irradiated, at which time free amino acids, or derivatives thereof, will be generated inside of the living tissues.

Still another object of the present invention is to provide a method for rapidly delivering controlled doses of amino acids, or derivatives thereof, to spatially restricted sites in living biological samples at physiological temperatures.

These and other objects of the present invention, which will be apparent from the detailed description of the invention provided hereinafter, have been met by a compound represented by Formulae (I), (II), (IV), (V), (VI) or (VII):

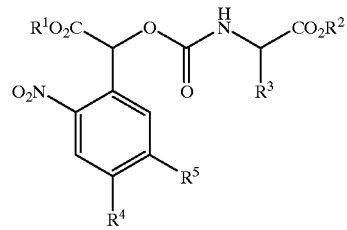

Formula (I)

wherein $R^1$ and $R^2$, which may be the same or different, are each selected from the group consisting of H, Li, Na, K, Cs, an alkyl having from 1 to 5 carbon atoms, $NH_4$, and $-CH_2O_2C-R^{1a}$, wherein $R^{1a}$ is an alkyl having from 1 to 5 carbon atoms; additionally, $R^2$ is selected from the group consisting of 3,4-dihydro-4-oxo-1,2,3-benzotriazin-3-yl, 2-nitrophenyl, 4-nitrophenyl, pentachlorophenyl, pentafluorophenyl, and N-succinimidyl; and wherein $R^3$ is selected from the group consisting of H, an alkyl having from 1 to 5 carbon atoms, $CH_3-S-(CH_2)_2-$, benzyl, and $-(CH_2)_n-(CO)-Y$, wherein n is an integer of from 1 to 5 and Y is $OR^{3a}$ or $NR^{3b}R^{3c}$, wherein $R^{3a}$, $R^{3b}$ and $R^{3c}$, which may be the same or different, are each selected from the group consisting of H and an alkyl having from 1 to 5 carbon atoms, and $R^{3a}$ may additionally be selected from the group consisting of Li, Na, K and Cs; and wherein $R^4$ and $R^5$, which may be the same or different, are each selected from the group consisting of H, an alkyl having from 1 to 5 carbon atoms, F, Cl, Br, CN, $NO_2$, $CO_2R^{4a}$, $OR^{4a}$, wherein $R^{4a}$ is selected from the group consisting of H, Li, Na, K, Cs, an alkyl having from 1 to 5 carbon atoms, $NH_4$, and $-CH_2O_2-R^{4b}$, wherein $R^{4b}$ is an alkyl having from 1 to 5 carbon atoms; and wherein optionally, $R^4$ and $R^5$ together from a methylenedioxy $(O-CH_2-O)$ linkage;

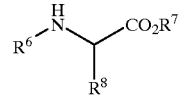

Formula (II)

wherein $R^6$ is selected from the group consisting of H, t-butyloxycarbonyl (Boc), benzyloxycarbonyl (Cbz), 9-fluorenylmethyloxycarbonyl (Fmoc), and a group represented by Formula (III);

wherein $R^7$ is selected from the group consisting of H, Li, Na, K, Cs, an alkyl having from 1 to 5 carbon atoms, $NH_4$ 3,4-dihydro-4-oxo-1,2,3-benzotriazin-3-yl, 2-nitrophenyl, 4-nitrophenyl, pentachlorophenyl, pentafluorophenyl, N-succinimidyl, and —CH$_2$O$_2$C—R$^{7a}$, wherein R$^{7a}$ is an alkyl having from 1 to 5 carbon atoms; and wherein R$^8$ is selected from the group consisting of —(CH$_{2-p}$(CH$_3$)$_p$)—Y—R$^{8a}$, —(CH$_{2-p}$(CH$_3$)$_p$)—C$_6$H$_4$—Y—R$^{8a}$, wherein p is 0, 1, or 2, Y is O or S, wherein R$^{8a}$ is a group represented by Formula (III) and —(CH$_2$)$_q$—Z, wherein q is 3 or 4, and Z is —NH—R$^{8b}$ or —NH—C(=NH)—NH—R$^{8b}$, wherein R$^{8b}$ is a group represented by Formula (III);

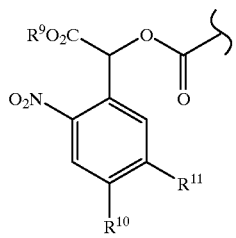

Formula (III)

wherein R$^9$ is selected from the group consisting of H, Li, Na, K, Cs, an alkyl having from 1 to 5 carbon atoms, NH$_4$, and —CH$_2$O$_2$C—R$^{9a}$, wherein R$^{9a}$ is an alkyl having from 1 to 5 carbon atoms; and wherein R$^{10}$ and R$^{11}$, which may be the same or different, are each selected from the group consisting of H, an alkyl having 1 to 5 carbon atoms, F, Cl, Br, CN, NO$_2$, CO$_2$R$^{10a}$, and OR$^{10a}$, wherein R$^{10a}$ is selected from the group consisting of H, Li, Na, K, Cs, an alkyl having from 1 to 5 carbon atoms, NH$_4$, and —CH$_2$O$_2$C—R$^{10b}$, wherein R$^{10b}$ is an alkyl having from 1 to 5 carbon atoms; and wherein optionally, R$^{10}$ and R$^{11}$ together form a methylenedioxy (O—CH$_2$—O) linkage;

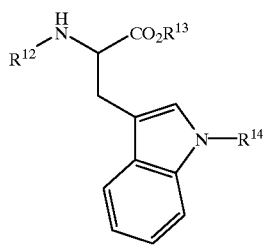

Formula (IV)

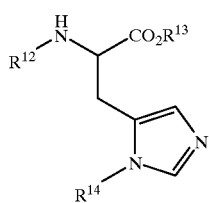

Formula (V)

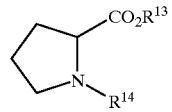

Formula (VI)

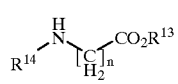

Formula (VII)

wherein R$^{12}$ is selected from the group consisting of H, t-butyloxycarbonyl (Boc), benzyloxycarbonyl (Cbz), 9-fluorenylmethyloxycarbonyl (Fmoc), and a group represented by Formula (III);

wherein R$^{13}$ is selected from the group consisting of H, Li, Na, K, Cs and an alkyl having from 1 to 5 carbon atoms, NH$_4$, 3,4-dihydro-4-oxo-1,2,3-benzotriazin-3-yl, 2-nitrophenyl, 4-nitrophenyl, pentachlorophenyl, pentafluorophenyl, and N-succinimidyl, and —CH$_2$O$_2$C—R$^{13a}$, wherein R$^{13a}$ is an alkyl having from 1 to 5 carbon atoms; and wherein R$^{14}$ is a group represented by Formula (III).

In another embodiment, the above-described objects of the present invention have been met by a method for producing a free amino acid or derivative thereof comprising the step of UV irradiating a compound represented by Formulae (I), (II), (IV), (V), (VI) or (VII).

BRIEF DESCRIPTION OF THE DRAWINGS

In FIG. 6, the trace shown is the sum of 16 individual pulse experiments; symbols (+) represent experimental data; and the solid curve through the data is the exponential fit to the data.

In FIG. 7, each trace is the average result from three patches, and vertical dotted lines delimit the duration of the UV pulses.

In FIG. 8 the double bars above the trace mark the duration of exposure to UV light; and the inset shows the molecular structure of N-Nmoc-L-glutamate.

In FIG. 9, the trace is displayed on an expanded time scale to show the pH-dependence of the kinetics more clearly; and vertical bars above the traces mark the shutter opening time course: the first bar marks initiation of shutter opening; the second bar marks the time at which the shutter is fully open; the third bar marks initiation of closure.

In FIG. 10A, the upper trace depicts the baseline current; and the arrow heads mark the time of reagent delivery. In FIG. 10B, each data point is the average peak current from a group tested; data are plotted as mean ± S.E.M.; where not shown, error bars are smaller than symbols; and solid lines are least-square fits to the data points.

FIG. 11 shows the reaction scheme for the synthesis of N-Nmoc-γ-aminobutyric acid.

DETAILED DESCRIPTION OF THE INVENTION

Figure 1:
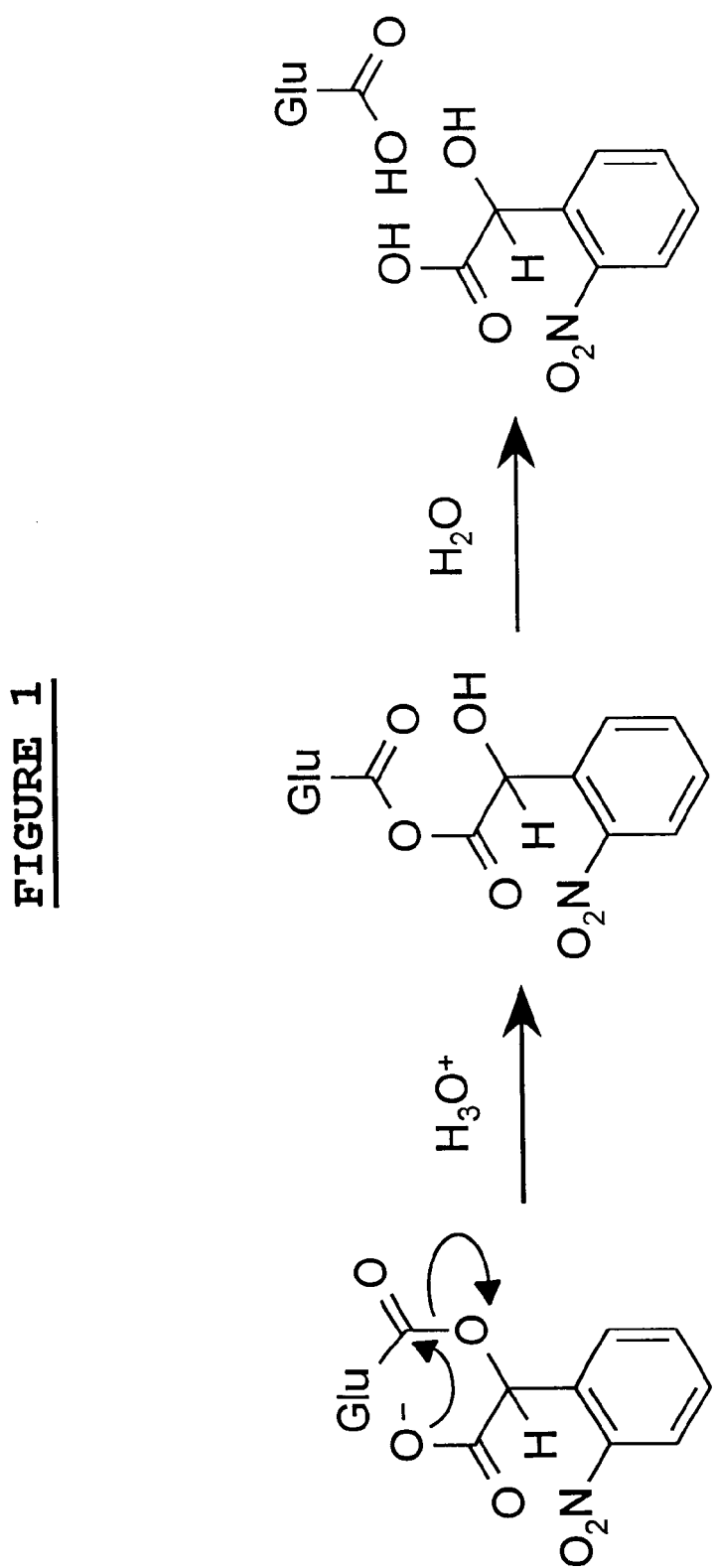
FIG. 1 shows the reaction scheme for the spontaneous hydrolysis of γ-CNB-Glu.
Figure 2:
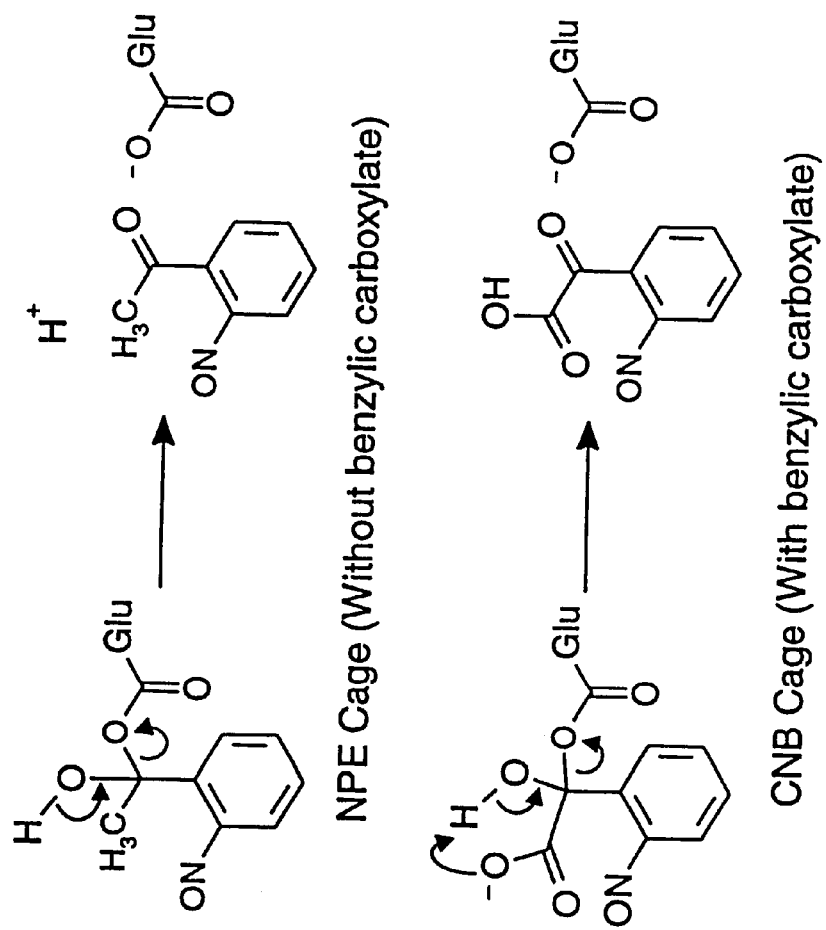
FIG. 2 shows a mechanistic comparison of the breakdown of the photochemically generated hemiacetal intermediates to release glutamate from the NPE and CNB cages.

As discussed above, in one embodiment, the above-described objects of the present invention have been met by a compound represented by Formulae (I) (II), (IV), (V), (VI) or (VII).

The compounds of the present invention are biologically inert, can be taken up by living cells and/or tissues will remain stable until irradiated, at which time free amino acid compound is released. Thus, a way of instantaneously generating intracellular and/or extracellular free amino acid or derivative thereof is made available by the compounds of the present invention.

In addition, by using a microscope, light can be narrowly focussed on a sample, even at the single cell level, so that highly localized administration of free amino acid compound can be achieved. Moreover, because light flashes can be very short and intense, free amino acid or derivative thereof can be generated at a precise instant with sub-second time resolution. In addition, varying doses of free amino acid or derivative thereof can be delivered by varying the intensity and/or duration of the light flashes, allowing dose-response relationships to be studied. The compounds of the present invention also exhibit little toxicity, and are easily loaded into living cells and/or tissues.

In Formulae (I)–(VII), the substituent groups are further defined as follows:

$R^1$ and $R^2$ are preferably each selected from the group consisting of H, Na, K, methyl, ethyl, and t-butyl.

$R^3$ is preferably selected from the group consisting of H, $CH_3$, $-CH(CH_3)_2$, $-CH_2-CH(CH_3)_2$, $-CH_2-CH(CH_3)(CH_2CH_3)$, $-CH_2CH_2SCH_3$, $-CH_2-C_6H_5$, $-CH_2CO_2H$, $-CH_2CONH_2$, $-CH_2CH_2CO_2H$, and $-CH_2CH_2CONH_2$.

$R^4$ and $R^5$ are preferably each H or $-OCH_3$, or combined together to form $-OCH_2O-$.

$R^6$ is preferably selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc).

$R^7$ is preferably selected from the group consisting of H, Na, K, methyl, ethyl, and t-butyl.

$R^8$ is preferably selected from the group consisting of (t-butyl-o-nitromandelyloxycarbonyl)$-OCH_2-$, (t-butyl-o-nitromandelyloxycarbonyl)-$OCH(CH_3)-$, (t-butyl-o-nitromandelyloxycarbonyl)-$SCH_2-$, (t-butyl-o-nitromandelyloxycarbonyl)-$NH(CH_2)_4-$, (t-butyl-o-nitromandelyloxycarbonyl)-$NH-C(=NH)-NH(CH_2)_3-$, and (t-butyl-o-nitromandelyloxycarbonyl)-$O-C_6H_4-CH_2-$.

$R^9$ is preferably selected from the group consisting of H, $CH_3$, and t-butyl.

$R^{10}$ and $R^{11}$ are preferably each H or $-OCH_3$, or combined together to form $-OCH_2O-$.

$R^{12}$ is preferably selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc).

$R^{13}$ is preferably selected from the group consisting of H, $CH_3$, and t-butyl.

$R^{14}$ is preferably t-butyl-o-nitromandelyloxycarbonyl (t-butyl Nmoc).

Acetoxymethyl ($-CH_2O_2CCH_3$) (AM) esters can be directly loaded into living cells. This is because these esters mask the negative charge on the carboxyl group, and the resulting compounds are neutral and hydrophobic, such that they easily diffuse across biological membranes. Once inside the cells, however, the esters are readily hydrolyzed by non-specific esterases to yield the caged amino acid compound, which are negatively charged, and unable to cross biological membranes, and thus become trapped and accumulate inside the cells.

Specific examples of the compounds of the present invention include N-(t-butyl Nmoc)-glycine, N-(t-butyl Nmoc)-L-alanine, N-(t-butyl Nmoc)-D-alanine, N-(t-butyl Nmoc)-L-valine, N-(t-butyl Nmoc)-D-valine, N-(t-butyl Nmoc)-L-leucine, N-(t-butyl Nmoc)-D-leucine, N-(t-butyl Nmoc)-L-isoleucine, N-(t-butyl Nmoc)-D-isoleucine, N-(t-butyl Nmoc)-L-methionine, N-(t-butyl Nmoc)-D-methionine, N-(t-butyl Nmoc)-L-phenylalanine, N-(t-butyl Nmoc)-D-phenylalanine, α-N-(t-butyl Nmoc)-L-aspartic acid, α-N-(t-butyl Nmoc)-D-aspartic acid, α-N-(t-butyl Nmoc)-L-asparagine, α-N-(t-butyl Nmoc)-D-asparagine, α-N-(t-butyl Nmoc)-L-glutamic acid, α-N-(t-butyl Nmoc)-D-glutamic acid, α-N-(t-butyl Nmoc)-L-glutamine, α-N-(t-butyl Nmoc)-D-glutamine, N-(t-butyl Nmoc)-L-proline, N-(t-butyl Nmoc)-D-proline, α-N-Fmoc-ε-N-(t-butyl Nmoc)-L-lysine, α-N-Fmoc-ε-N-(t-butyl Nmoc)-D-lysine, α-N-Fmoc-$N^G$-(t-butyl Nmoc)-L-arginine, α-N-Fmoc-$N^G$-(t-butyl Nmoc)-D-arginine, α-N-Fmoc-S-(t-butyl Nmoc)-L-cysteine, α-N-Fmoc-S-(t-butyl Nmoc)-D-cysteine, α-N-Fmoc-β-O-(t-butyl Nmoc)-L-serine, α-N-Fmoc-β-O-(t-butyl Nmoc)-D-serine, α-N-Fmoc-β-O-(t-butyl Nmoc)-L-threonine, α-N-Fmoc-β-O-(t-butyl Nmoc)-D-threonine, α-N-Fmoc-4-O-(t-butyl Nmoc)-L-tyrosine, α-N-Fmoc-4-O-(t-butyl Nmoc)-D-tyrosine, α-N-Fmoc-$N^{Im}$-(t-butyl Nmoc)-L-tryptophan, α-N-Fmoc-$N^{Im}$-(t-butyl Nmoc)-D-tryptophan, α-N-Fmoc-$N^{Im}$-(t-butyl Nmoc)-L-histidine, α-N-Fmoc-$N^{Im}$-(t-butyl Nmoc)-D-histidine, N-Nmoc-glycine, N-Nmoc-L-alanine, N-Nmoc-D-alanine, N-Nmoc-L-valine, N-Nmoc-D-valine, N-Nmoc-L-leucine, N-Nmoc-D-leucine, N-Nmoc-L-isoleucine, N-Nmoc-D-isoleucine, N-Nmoc-L-methionine, N-Nmoc-D-methionine, N-Nmoc-L-phenylalanine, N-Nmoc-D-phenylalanine, α-N-Nmoc-L-aspartic acid, α-N-Nmoc-D-aspartic acid, α-N-Nmoc-L-asparagine, α-N-Nmoc-D-asparagine, α-N-Nmoc-L-glutamic acid, α-N-Nmoc-D-glutamic acid, α-N-Nmoc-L-glutamine, α-N-Nmoc-D-glutamine, N-Nmoc-L-proline, N-Nmoc-D-proline, ε-N-Nmoc-L-lysine, ε-N-Nmoc-D-lysine, $N^G$-Nmoc-L-arginine, $N^G$-Nmoc-D-arginine, S-Nmoc-L-cysteine, S-Nmoc-D-cysteine, β-O-Nmoc-L-serine, β-O-Nmoc-D-serine, β-O-Nmoc-L-threonine, β-O-Nmoc-D-threonine, 4-O-Nmoc-L-tyrosine, 4-O-Nmoc-D-tyrosine, $N^{Im}$-Nmoc-L-tryptophan, $N^{Im}$-Nmoc-D-tryptophan, $N^{Im}$-Nmoc-L-histidine, $N^{Im}$-Nmoc-D-histidine, and N-Nmoc-4-aminobutyric acid.

UV light generally is considered to have a wavelength of 200 to 400 nm. In the present invention, any light within this wavelength range can be employed. However, from the standpoint of biological compatibility, it is preferred that the wavelength employed be in the range of 300 to 400 nm, as UV at wavelengths below 300 nm can damage proteins and nucleic acids in cells.

The temperature at which UV illumination is carried out is not critical to the present invention, and can be any temperature which does not adversely affect living cells. Generally, illumination is carried out at about 10 to 40° C.

The duration of UV illumination is not critical to the present invention, and will depend upon the intensity of the light source. Examples of such light sources include a mercury lamp and a xenon lamp.

The compounds of the present invention can be used in the method of present invention in the form of an aqueous solution. The concentration of the compounds of the present invention in the aqueous solution is not critical to the present invention. Generally, the concentration will be about $10^{-5}$ to $10^{-1}$ M.

The pH of the aqueous solution is not critical to the present invention, and generally is about 6 to 8.

The pH can be maintained using any suitable buffering system, such as a phosphate or N'-2-hydroxyethlypiperazine-N'-2-ethanesulfonate (HEPES) buffer.

The compounds of the present invention can be used in an aqueous bath of culture media so as to perfuse tissues or cultured cells. UV illumination of the culture medium bathing the tissue or cells liberates free amino acid or derivative thereof, which readily crosses biological membranes, and can thus enter the cells.

Alternatively, an aqueous solution of the compounds of the present invention can be introduced into living cells through either microinjection or patch pipets. The caged amino acid or derivative thereof, when charged, is retained in the injected cells. Flashing the cells with UV light will generate an amino acid or derivative thereof from within loaded cells.

Alternatively, the compounds of the present invention can be passively loaded into cells through incubation with the corresponding AM ester. Flashing the cells with UV light will generate free amino acid or derivative thereof from within the loaded cells.

The compounds of the present invention can be prepared in general by ester formation between a protected and activated caging group (e.g., methyl-2-[2-nitrophenyl] acetate-2-oxycarbonylimidazole or t-butyl-2-[2-nitrophenyl]acetate-2 -oxycarbonylimidazole) with an amino acid (or derivative thereof). The methyl- or t-butyl-protected carboxyl function in the resulting product can be converted to other forms through de-esterification and/or re-esterification.

Conventional means for rapidly delivering drugs or reagents to living cells typically involves superfusing a solution containing the desired drug or reagent over the cells. The speed of delivery is limited by two factors: (1) the rate at which an aqueous solution can flow through the experimental chamber containing the living cells, and (2) the rate at which the drug or reagent molecules are able to penetrate into the interior of cells. Such rate limitations imply that reagent application by superfusion usually gives rise to a delay between reagent application and the elicited response from a living cell. Directly generating a reagent or drug in situ by photolysis of caged molecules trapped within cells eliminates the rate limitations inherent to superfusion and, therefore, can elicit much faster responses.

Nmoc-amino acid or derivative thereof (e.g., Nmoc-Glu) has utility in applications where its major advantages (low pre-photolysis activity and high hydrolytic stability) are most useful. Such applications include:

(1) studies where the caged amino acid or derivative thereof (e.g., glutamate) needs to be kept in aqueous solution near neutral pH for extended periods of time;

(2) studies where background activation of cells or tissues needs to be minimized (for example, this is particularly important for neuronal NMDA GluRs, which require only micromolar levels of free glutamate for activation);

(3) studies where desensitization of biological responses (e.g., non-NMDA GluR channels) needs to be minimized;

(4) studies where the absolute amplitude of the biological responses (e.g., non-NMDA GluR response) is important; and (5) studies where the concentration of photoreleased amino acid or derivative thereof (e.g., free glutamate) must be high (e.g., in the mM range).

In view of the foregoing, Nmoc-amino acid (e.g., Nmoc-Glu) is believed to useful in brain slices, such as in studies that use photostimulation to analyze brain circuitry (Callaway et al, *Proc. Natl. Acad. Sci., USA.*, 90:7661–7665 (1993); and Katz et al, supra). Residual pre-photolysis activity, even if low by chemical measures (e.g.,<1% free glutamate), may still cause significant distortion of neuronal circuit properties. Micromolar levels of free glutamate may activate NMDA GluRs on non-targeted neurons (Mayer et al, supra), and may desensitize non-NMDA GluRs of the relevant neuronal circuit (Trussell et al, supra). Therefore, it is believed that in such studies, the low pre-photolysis activity of Nmoc-Glu will help minimize background activation of non-targeted neurons and maintain optimal responsiveness of the stimulated circuit.

Another application of Nmoc-Glu is believed to be in experiments where it is advantageous to isolate the response of the non-NMDA subset of GluRs to the exclusion of other membrane conductances. For example, in order to quantitatively map the distribution of functional non-NMDA GluRs on the dendrite, it would be necessary to achieve saturating concentrations of free glutamate following photolysis without triggering receptor desensitization before photolysis. It would also be necessary to eliminate activation of NMDA GluR channels and voltage-gated calcium channels on the dendrite. Decreasing extracellular pH will increase the rate of glutamate photorelease from Nmoc-Glu without significantly affecting the gating properties of non-NMDA GluRs (Tang et al, *Proc. Natl. Acad. Sci., U.S.A.*, 87:6445–6449 (1990)). Decreasing extracellular pH would also down-regulate voltage-gated calcium channels (Iijima et al, *Proc. Natl. Acad. Sci., U.S.A.*, 83:654–658 (1986)) and NMDA GluR channels (Tang et al, supra (1990))—two conductances which may be inadvertently recruited with strong dendritic stimulation. These considerations, combined with the low residual activity of Nmoc-Glu, suggest that rapid focal photolysis of Nmoc-Glu at millimolar concentrations in an acidic environment may provide the ideal means for quantitatively mapping the distribution of non-NMDA GluRs.

Caged amino acid or derivative thereof as embodied by the compounds represented by Formulae (I), (II), (IV), (V), (VI) or (VII) are also expected to be useful in the manual and automated synthesis of caged peptides, i.e., peptides whose biological activity is temporarily blocked by the presence of a cage, but which biological activity can be restored by exposure to UV light. Being able routinely to synthesize caged peptides expands the biologist's experimental repertoire to include the ability to manipulate living biological specimens through controlled photorelease of peptide effector is molecules.

The following examples are provided for illustrative purposes only and are in no way intended to limit the scope of the present invention.

In the following Synthesis Examples, the reagents and solvents were ACS or HPLC grade and were used as received from Aldrich Chemical Company (Milwaukee, Wis.) or Fisher Scientific (Pittsburgh, Pa.). N,N- dimethylformamide (DMF) and dichloromethane were stored over 3 Å molecular sieves.

All oxygen- and water-sensitive reactions were performed under dry argon atmosphere. For water-sensitive reactions, glassware was dried at 130° C. for at least 3 hr, and cooled under a stream of argon or in a desiccator prior to use.

The products were purified by column chromatography as described by Still et al, *J. Org. Chem.*, 43:2923 (1978), using silica gel 60 (230–400 mesh, E. Merck).

Melting points were recorded on a Melt-temp II (Laboratory Devices) apparatus coupled to an Omega (Omega Engineering) HH23 digital thermometer. All of the melting points reported were uncorrected.

The structures of all of the purified products were established by NMR spectral analysis. Spectra were recorded on a General Electric QE-300 (300 MHZ) NMR spectrometer. All of the samples were dissolved in $CDCl_3$ (0.03% (w/v) tetramethylsilane (TMS)) unless otherwise stated, and were referenced to TMS. Samples in solvents other than $CDCl_3$ were referenced to the residual solvent peak. Resonances are reported in the following format: NMR (solvent): chemical shift in ppm downfield from tetramethylsilane, multiplicity (s=singlet, d=doublet, t=triplet, q=quartet, m=multiplet, b=broad), spin-spin coupling constant if appropriate, and integrated number of protons. High resolution mass spectrometric analysis (HRMS), by electron impact (EI), chemical ionization (CI), or fast-atom bombardment (FAB), was performed at the University of Maryland, College Park, on a Model VG707E spectrometer (VG Analytical).

Synthesis Example 1

N-[2-[2-nitrophenyl]-2-oxycarbonyl acetic acid]-(S)-glutamic acid

Simple o-nitrobenzyl carbamates are quite chemically stable to hydrolysis even under moderately strong acidic or basic aqueous conditions (Greene et al, supra), and thus provide a good avenue for making a chemically stable caged glutamate. It has been reported, however, that the o-nitrobenzyl carbamate of glutamate photolyzes only slowly near physiological pH ($t_{1/2}$=50 ms at pH 7; Corrie et al, supra). Hess and colleagues had shown that introducing a carboxyl group at the benzylic position of the o-nitrobenzyl system to give the α-CNB group significantly increases the photolysis rate (Milburn et al, *Biochem.*, 28:49–55 (1989); Billington et al, *Biochem.*, 31:5500–5507 (1992); Gee et al, *J. Am. Chem. Soc.*, 116:8366–8367 (1994); Gee et al, J. Org. Chem., 60:4260–4263 (1995); Wieboldt et al, supra (1994a); and Wieboldt et al, *Biochem.*, 33:1526–1533 (1994b)). Reasoning from the foregoing, the o-nitromandelyloxycarbonyl (Nmoc) group (Rossi et al, *J. Biol. Chem.*, 272:3266–3271 (1997)), which is designed to combine the rate-enhancing effect of the benzylic carboxyl group with the known stability of carbamate linkages, was employed.

Initial attempts to synthesize N-Nmoc-L-glutamate relied on the previously prepared methyl ester of the Nmoc-imidazole caging reagent (Rossi et al, supra). When the di-t-butyl ester of L-glutamic acid was allowed to react with methyl Nmoc-imidazole, however, the major product isolated was an oxazolidinone, rather than the desired caged glutamate. It was found in the present invention that this unwanted reaction could be suppressed by using the t-butyl ester of Nmoc-imidazole, instead. The preparation of t-butyl Nmoc-imidazole (Compound) and N-Nmoc-L-glutamate (Compound 1) is shown in FIG. 4.

Figure 4:
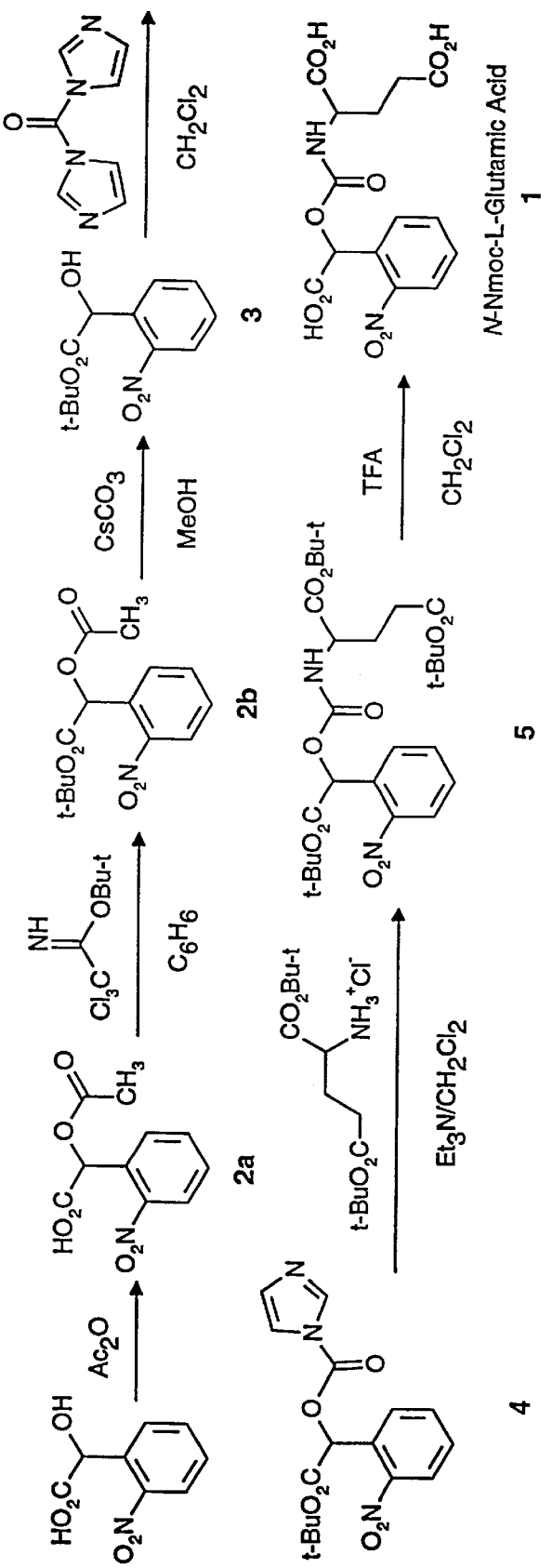
FIG. 4 shows the reaction scheme for the synthesis of Nmoc-Glu.

In particular in FIG. 4, o-nitromandelic acid is first protected on the hydroxyl by acetylation (Compound 2a), converted to the t-butyl ester (Compound 2b), deacetylated (Compound 3), reacted with carbonyldimidazole to yield the active reagent (Compound 4), which is use to react with (S)-glutamic acid di-t-butyl ester hydrochloride, to give the fully protected caged molecule (Compound 5), which is finally deprotected with trifluoroacetic acid to yield the desired caged reagent, N-Nmoc-L-glutaminic acid (Compound 1).

More specifically, 2-acetoxy-2-[2-nitrophenyl]-acetic acid (FIG. 4; Compound 2a)) was prepared by refluxing o-nitromandelic acid (Rossi et al, supra) (7.88 g, 40 mmol) in acetic anhydride (60 ml, 640 mmol) for 45 min. The reaction mixture was cooled to room temperature and diluted with tetrahydrofuran (THF) (50 ml) and water (50 ml). After stirring for 2 hr, the aqueous layer was removed, the organic layer was diluted with toluene (100 ml), and extracted with water (2×100 ml). The organic layer was dried over $MgSO_4$, and the solvent was evaporated to give a brown oil that was use to prepare to Compound 2b without further purification. t-butyl 2-acetoxy-2-[2-nitrophenyl]-acetate (FIG. 4; Compound 2b) was prepared by adding t-butyl-trichloro-acetimidate (8.74 g, 40 mmol) to a solution of Compound 2a in benzene (50 ml). The reaction was stirred for 1 hr, and the solid was removed by filtration. The filtrate was concentrated and chromatographed with hexane/ethyl acetate (5:1) to give 7.41 g (63%) of Compound 3 as an oil. $^1$H NMR: 8.02 (d, J=8.1 Hz, 1H), 7.65 (d, J=3.9 Hz, 1H), 7.56–7.51 (m, 2H), 6.75 (s, 1H), 2.21 (s, 3H), 1.40 (s, 9H). High resolution mass spectrometry chemical ionization (mass spectrometry) (HMRS-CI): calculated for $C_{14}H_{18}NO_6$ $[M^++H]$m/z=296.1134, observed 296.1122.

t-butyl 2-hydroxy-2-[2-nitrophenyl]acetate (FIG. 4; Compound 3) was prepared by adding cesium carbonate (0.365 g, 1.12 mmol) to a solution of Compound 2b (6.63 g, 22.4 mmol) in methanol (50 ml). After 1 hr, the solution was diluted with ethyl acetate (100 ml) and passed through a plug of silica gel (15 g). Evaporation of solvent from the eluate gave 5.36 g (94%) of Compound 3 as an oil. $^1$H NMR: 7.96 (dd, J=1.2, 6.8 Hz, 1H), 7.72–7.60 (m, 2H), 7.51–7.45 (m, 1H), 5.84 (d, J=3.7 Hz, 1H), 3.67 (br d, J=4.4 Hz, 1H), 1.38 (s, 9H). HRMS(CI): calculated for $C_{12}H_{16}NO_5$ $[M^++H]$m/z=254.1028, observed 254.1029.

t-butyl 2-[2-nitrophenyl]-2-[oxycarbonylimidazole] acetate (FIG. 4; Compound 4) was prepared by dissolving carbonyl-diimidazole (1.30 g, 8.00 mmol) and Compound 3 (2.02 g, 8.00 mmol) in methylene chloride (25 ml). After 1 hr, the reaction mixture was washed with water (3×25 ml), and dried over $MgSO_4$. The solvent was evaporated and the residue was chromatographed with hexane/ethyl acetate (3:2) to give 2.15 g (77%) of Compound 4 as an oil. $^1$HNMR: 8.20 (s, 1H), 8.11 (dd, J=1.3, 6.6 Hz, 1H), 7.73–7.63, (m, 3H), 7.48 (s, 1H), 7.11 (s, 1H), 6.88 (s, 1H), 1.43 (s, 9H). HRMS(CI) calculated for $C_{16}H_{18}N_3O_6$ $[M^++H]$m/z=348.1196, observed 348.1194.

N-t-butyl 2-[2-nitrophenyl]-2-oxycarbonyl acetate]-(S)-glutamic acid, di-t-butyl ester (FIG. 4; Compound 5) was prepared by dissolving (S)-glutamic acid di-t-butyl ester hydrochloride (0.736 g, 2.49 mmol) and Compound 4 (0.866 g, 2.49 mmol) in methylene chloride (10 ml). Triethyl amine (0.35 ml, 2.5 mmol) was then added, and the reaction mixture was stirred for 40 hr. The solvent was removed by evaporation, and the residue was chromatographed with hexane/ethyl acetate (5:1) to give 0.858 g (64%) of Compound 5. $^1$HNMR: 8.00, (d, J=7.82 Hz, 1H), 7.65–7.62 (m, 2H), 7.53–7.47 (m, 1H), 6.72 (s, 0.5H), 6.68 (s, 0.5H), 5.64–5.58 (m, 1H), 4.29–4.21 (m, 1H), 2.32–2.08 (m, 4H), 1.93–1.87 (m, 2H), 1.57 (s, 4.5H), 1.54 (s, 4.5H), 1.47 (s, 4.5H), 1.44 (s, 4.5H), 1.43 (s, 4.5H), 1.42 (s, 4.5H). HRMS (CI) calculated for $C_{26}H_{39}N_2O_{10}$ [$M^++H$]m/z=539.2605, observed 539.2580.

N-[2-[2-nitrophenyl]-2-oxycarbonyl acetic acid]-(S)-glutamic acid (N-Nmoc-L-glutamic acid) (FIG. 4; Compound 1) was prepared by adding triester Compound 5 (0.475 g, 0.882 mmol) to a mixture of methylene chloride (5.0 ml) and trifluoroacetic acid (TFA) (5.0 ml). After 2 hr, the solvent was removed by evaporation. Azeotropic removal of residual acid with benzene gave 0.320 g (98%) of Compound 1. High resolution electron impact (mass spectrometry) (HRMS-EI) calculated for $C_{14}H_{14}N_2O_{10}$ [$M^+$]m/z=370.0649, observed 370.0635.

Synthesis Example 2

N-Nmoc-γ-aminobutyric acid

FIG. 11 shows the reaction scheme for the synthesis of N-Nmoc-γ-aminobutyric acid, where γ-aminobutyric acid reacts with t-butyl-Nmoc-imidazole (Compound 4 of FIG. 4) to produce N-(t-butyl-Nmoc)-γ-aminobutyric acid, which is then deprotected to yield N-Nmoc-γ-aminobutyric acid.

More specifically, N-[t-butyl-(2-nitromandelyl) oxycarbonyl]-4-aminobutyric acid (FIG. 11, Compound 9) was prepared by first dissolving 4-Aminobutyric acid (a.k.a. γ-aminobutyric acid, or GABA) (0.195 g, 1.89 mmol) and triethylamine (0.527 ml, 3.78 mmol) in 3.3 ml of DMF. Compound 4 of FIG. 4 (0.328 g, 0.944 mmol) was then added as a solution in 2.3 ml of DMF to the stirred reaction mixture. After 24 hr, the temperature was raised to 40° C. for 4 hr; thereafter, the reaction mixture was again stirred at room temperature overnight. The reaction mixture was diluted with 75 ml ethyl acetate, extracted with 0.5 M sodium citrate buffer (pH 4.5) (3×15 ml), dried over $MgSO_4$, and concentrated on a rotary evaporator. The crude product was chromatographed in hexane/ethyl acetate (1:2) containing 0.5% (v/v) acetic acid to yield a straw-colored oil, which subsequently crystallized. Yield was 0.251 g (70%). $^1$HNMR: 8.00, (d, J=7.82 Hz, 1H), 7.63 (m, 2H), 7.51 (m, 1H), 6.68 (s, 1H), 5.24 (m, 1H), 3.28 (m, 2H), 3.42 (m, 2H), 1.86 (m, 2H), 1.40 (s, 9H). HRMS (FAB) calculated for $C_{17}H_{23}O_8N_2$ [$M^++H$]m/z=383.14545, observed 383.14505.

N-[(2-nitromandelyl)oxycarbonyl]-4-aminobutyric acid (FIG. 11, Compound 10) was prepared by first dissolving Compound 9 of FIG. 1 (0.060 g, 0.157 mmol) in 10.5 ml of $CH_2Cl_2$. Trifluoroacetic acid (10.5 ml) was then added. After being stirred overnight, the reaction mixture was concentrated on a rotary evaporator, and chromatographed in hexane/ethyl acetate (1:5, containing 2.0% (v/v) acetic acid) to give the product, which was lyophilized from water to yield 0.0387 g (93%). $^1$HNMR (acetone-$d_6$): 8.07 (d, J=8.06, 1H), 7.55–7.90 (m, 3H), 6.78 (s, 1H), 3.79–5.90 (b, 1H), 3.22 (t, J=6.60, 2H), 2.37 (t, J=7.32, 2H), 1.81 (m, 2H). HRMS(FAB) calculated for $C_{13}H_{15}O_8N_2$ [$M^++H$]m/z=327.08286, observed 327.08228.

Synthesis Example 3

ε-N-[t-butyl-(2-nitromandelyl) oxycarbonyl]-L-lysine

Figure 12:
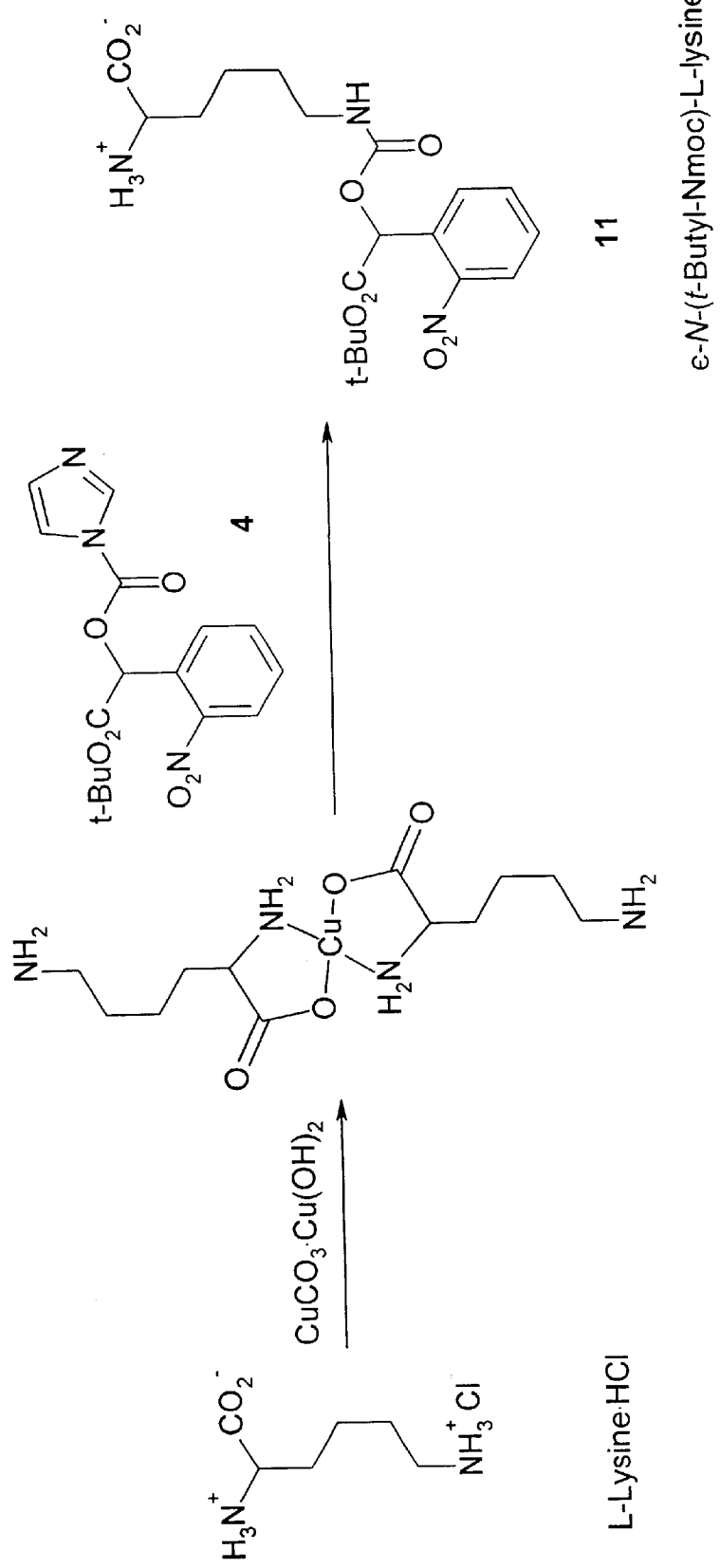
FIG. 12 shows the reaction scheme for the synthesis of ε-N-(t-butyl-Nmoc)-L-lysine.

FIG. 12 shows the reaction scheme for the synthesis of ε-N-[t-butyl-(2-nitromandelyl) oxycarbonyl]-L-lysine, where the cupric complex of L-lysine is first prepared and then reacted with t-butyl-Nmoc-imidazole (Compound 4 of FIG. 4) to produce ε-N-[t-butyl-(2-nitromandelyl) oxycarbonyl]-L-lysine.

More specifically, ε-N-[t-butyl-(2-nitromandelyl) oxycarbonyl]-L-lysine (FIG. 12, Compound 11) was prepared by the following procedure. An aqueous mixture of L-lysine hydrochloride (0.491 g, 2.69 mmol) and basic copper carbonate ($CuCO_3 \cdot Cu(OH)_2$, 0.807 g, 3.65 mmol) in 22 ml water was refluxed for 2 hr. The solution was filtered, and filtered solids were washed with 3.0 ml of water. The combined filtrate solution was concentrated to one half of initial volume on a rotary evaporator. $NaHCO_3$ (0.861, 10.2 mmol) was dissolved in the solution. The solution was stirred vigorously while Compound 4 of FIG. 4 (1.168 g, 3.363 mmol) was added gradually as a solution in 13 ml of acetone through an addition funnel, whereupon, a precipitate started to form. The reaction mixture was stirred overnight at room temperature, and then placed on a rotary evaporator to remove acetone. The precipitate in the reaction mixture was filtered and washed successively with water and ethyl ether. A suspension of the precipitate in water was stirred vigorously as a stream of $H_2S$ gas was introduced, whereupon, a dark precipitate started to appear. After 3 hr, the reaction mixture was evacuated to remove excess $H_2S$, and CuS precipitate was removed by filtration. The filtrate was concentrated on a rotary evaporator and lyophilized to give crude product as a yellowish powder. The crude product was chromatographed in $CHCl_3$/methanol/acetic acid (16:3:1) to yield 0.223 g (20%) of ε-N-[t-butyl-(2-nitromandelyl)oxycarbonyl]-L-lysine. $^1$HNMR: 8.01 (d, J=12.09), 7.75 (d, J=7.33, 2H), 7.23–7.65 (m, 9H), 6.67 (s, 1H), 5.61 (m, 1H), 5.24 (m, 1H), 4.25–4.60 (m, 3H), 4.20 (m, 1H), 3.20 (m, 4H), 1.60–2.00 (m, 2H), 1.49–1.60 (m, 2H), 1.39 (s, 9H). HRMS(FAB) calculated for $C_{19}H_{28}O_8N_3$ [$M^++H$]m/z=426.18765, observed 426.18470.

Figure 13:
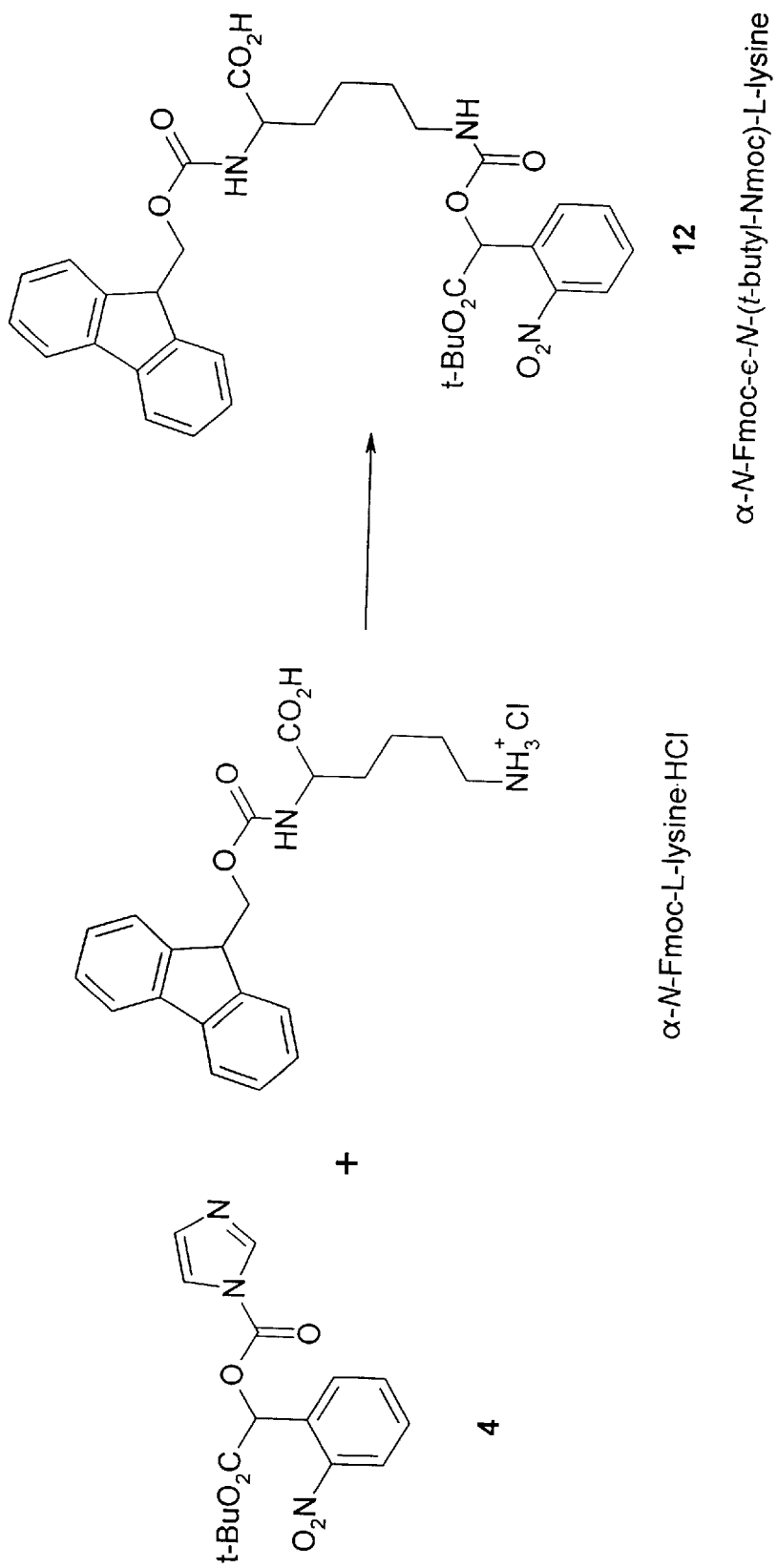
FIG. 13 shows the reaction scheme for the synthesis of α-N-Fmoc-ε-N-Fmoc-N-(t-butyl-Nmoc)-L-lysine.

Synthesis Example 4

α-N-(9-fluorenylmethyloxycarbonyl)-ε-N-[t-butyl-(2-nitromandelyl)oxycarbonyl]-L-lysine FIG. 13 shows the reaction scheme for the synthesis of α-N-(9-fluorenylmethyloxycarbonyl)-ε-N-[t-butyl-(2-nitromandelyl)oxycarbonyl]-L-lysine, where α-N-(9-fluorenylmethyloxycarbonyl)-L-lysine was reacted with t-butyl-Nmoc-imidazole (Compound 4 of FIG. 4) to produce α-N-(9-fluorenylmethyloxycarbonyl)-ε-N-[t-butyl-(2-nitromandelyl)oxycarbonyl]-L-lysine.

More specifically α-N-(9-fluorenylmethyloxycarbonyl)-ε-N-[t-butyl-(2-nitromandelyl)oxycarbonyl]-L-lysine (FIG. 13, Compound 12) was prepared by first dissolving α-N-(9-fluorenylmethyloxycarbonyl)-L-lysine hydrochloride (0.180 g, 0.444 mmol) and Compound 4 of FIG. 4 (0.185 g, 0.533 mmol) in 1.0 ml of DMF. To this solution, 1 equivalent of triethylamine (0.062 ml, 0.444 mmol) was added. A second equivalent of triethylamine was dissolved in 1.0 ml of DMF and added to the stirred reaction mixture through a dropping funnel at a rate of ~1 drop/10 min. Stirring was continued overnight. The reaction mixture was filtered to remove precipitates that had formed. The filtrate was mixed with 5.0 ml of water and stirred for 2 hr. 0.5 M Sodium citrate buffer (pH 4.5) (5.0 ml), was added and a new precipitate formed. The mixture was extracted with benzene (3×20 ml), and the combined organic extracts were dried ($Na_2SO_4$), filtered, and concentrated on a rotary evaporator. The crude product thus obtained was chromatographed in $CHCl_3$/methanol/acetic acid (97:2.5:0.5) to yield a yellow oil, which was dissolved in a small amount of toluene and evaporated to remove residual acetic acid azeotropically. The product was finally lyophilized from benzene to yield a white powder (0.127 9 (44%). HRMS(FAB) calculated for $C_{34}H_{38}O_{10}N_3$ [$M^++H$]m/z=648.25574, observed 648.25261.

In the following examples, the caged compounds were stored as dry powders at −20° C. Aqueous solutions of the caged compounds were kept acidic and were adjusted to physiological pH just prior to use, because neutralization of γ-O-α-carboxy-2-nitrobenzyl-glutamate greatly accelerates the rate of spontaneous hydrolysis. Following final dilution and pH adjustment, the solutions were kept at 0° C., and protected from light.

EXAMPLE 1

Photoreactivity of Nmoc-Glu

To demonstrate the photorelease yield of Nmoc-Glu, UV-visible absorption spectra were acquired from a solution of the sodium salt of Nmoc-Glu before and after being photolyzed with 365 nm light.

More specifically, using a stirred sample containing 149 $\mu$M of the sodium salt of Nmoc-Glu in 150 mM NaCl, 10 mM phosphate buffer (pH 7.2), UV-visible spectra were recorded after the stirred sample had been exposed for 0 and 1280 s to 365 nm light at a calibrated intensity of $8.6 \times 10^{-8}$ einst·cm$^{-2}$·s$^{-1}$. UV-visible spectra were recorded on a scanning spectrophotometer (Model Lambda 3B, Perkin-Elmer). Photolysis light intensity was determined by ferrioxalate actinometry (Rabek, *In: Experimental Methods in Photochemistry and Photophysics,* Interscience, Chichester, pages 944–946 (1982)). Output from a 100 W mercury arc lamp (HBO100; Osram, Danvers, Mass.), filtered through 3 mm UG-1 glass to isolate the 365 nm emission, was used for photolysis. The results are shown in FIG. 5A.

Figure 3:
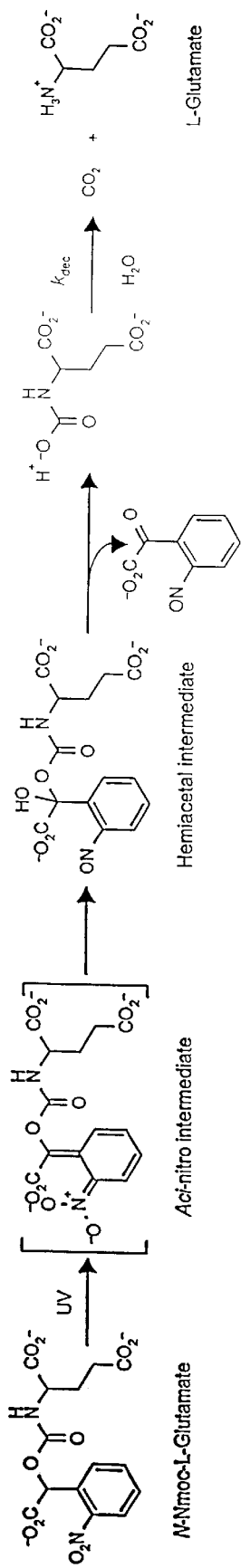
FIG. 3 shows the reaction scheme for the photolysis of Nmoc-Glu.
Figure 5A:
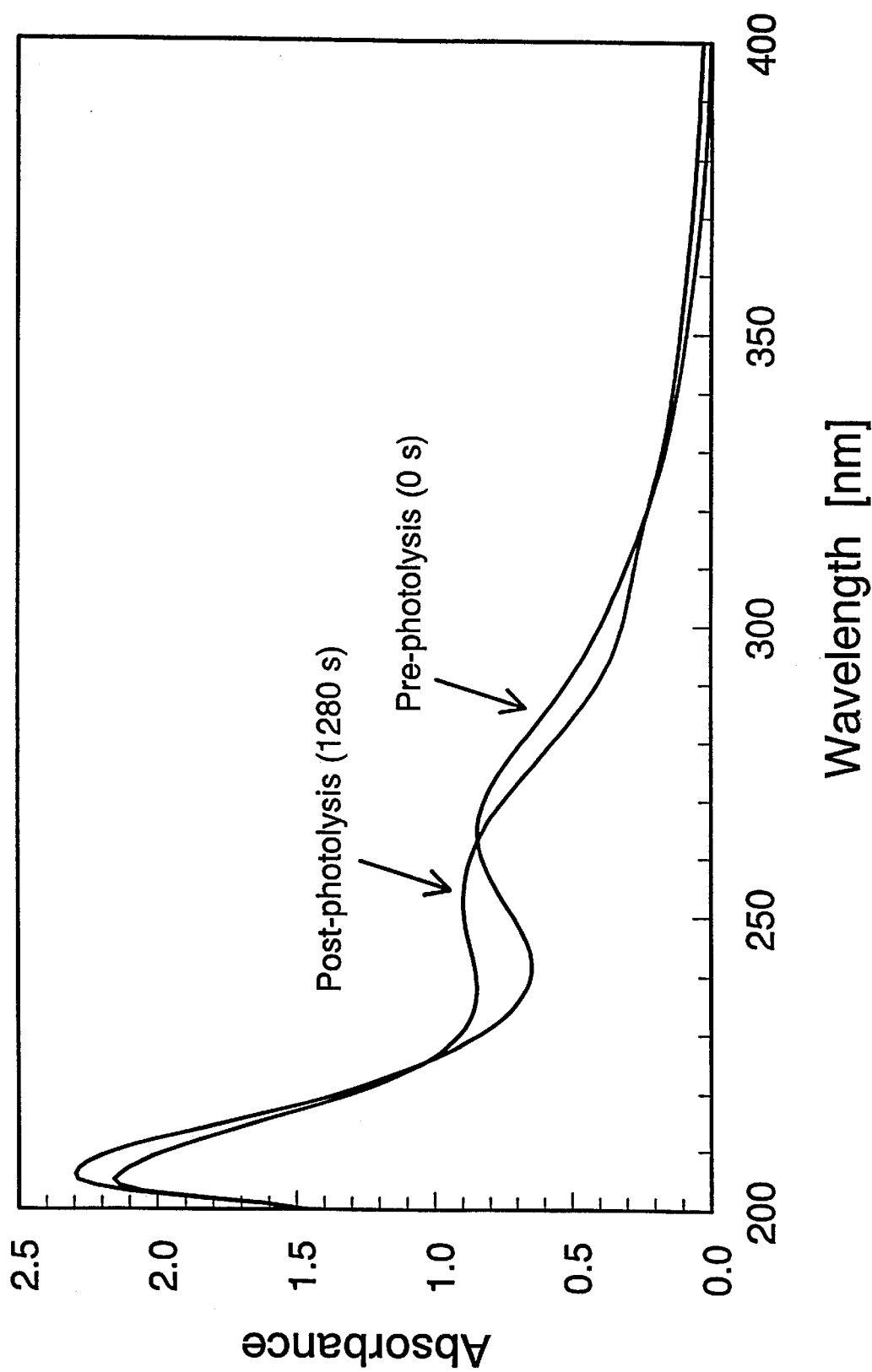
FIGS. 5A–5B show UV-visible absorption spectra of Nmoc-Glu pre- and post-photolysis (FIG. 5A); and of an exponential time course of steady-state photolysis of Nmoc-Glu (FIG. 5B).

As shown in FIG. 5A, the post-photolysis spectrum shows increased absorbance at longer wavelengths (>340 nm), which is consistent with the nitrosoketone side-product (FIG. 3; Compound 7) being more highly conjugated than the parent chromophore. The spectra showing the photolability of Nmoc-Glu are consistent with the known photochemical behavior of similar nitrobenzyl systems.

Because the spectra show good isosbestic points through the course of photolysis, the quantum efficiency of photolysis of Nmoc-Glu was next determined by analyzing the absorbance changes as a function of time. Determination of quantum yield (Q) of photolysis from UV-visible spectra collected after intervals of photolysis with a calibrated UV source was performed as described by Adams et al, *J. Am. Chem. Soc.*, 110:3212–3220 (1988); and Livingston et al, *In: Techniques of Chemistry., Vol. 3: Photochromism,* Brown, G. H., Ed., Wiley, New York, pages 13–44 (1971). The results are shown in FIG. 5B.

Figure 5B:
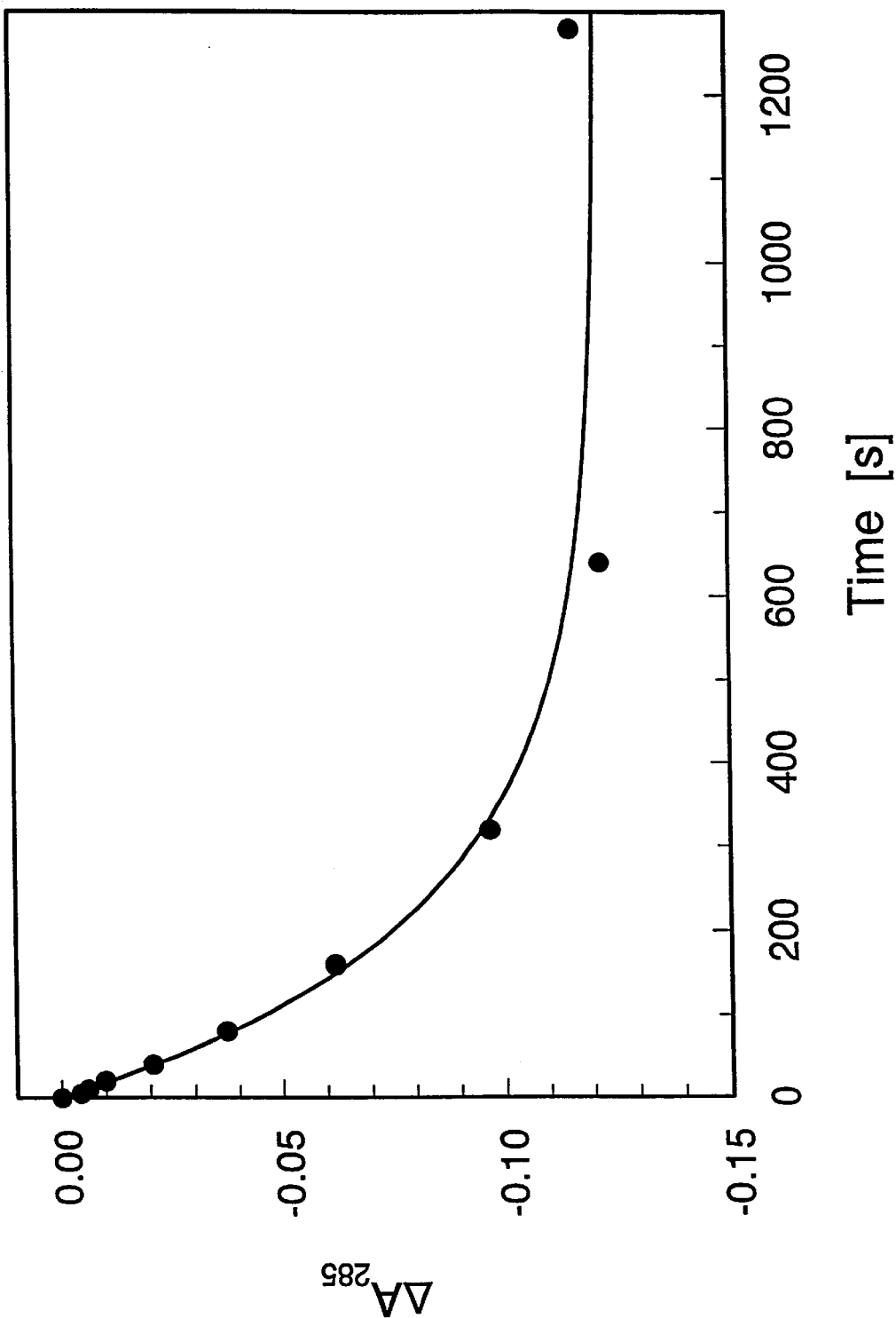

FIG. 5B shows a graph of $\Delta A_{285}$, the change in absorbance of the sample at 285 nm, as a function of time of photolysis by light of known intensity $I_0$. The data are well fit by a single exponential with $t_{1/e}=196\pm40$ s. The quantum yield of photolysis ($\phi$) of Nmoc-Glu was thus determined to be $\phi=2.303 I_0 \epsilon_{365} t_{1/e}=0.11$ (Adams et al, supra (1988); and Livingston, supra).

Next, the photocleavage kinetics of the caging group were examined by monitoring the transient absorbance changes characteristic of the short-lived aci-nitro intermediate (FIG. 3; Compound 6) (Schupp et al, *J. Photochem.*, 36:85–97 (1987); Yip et al, *J. Phys. Chem.*, 89:5328–5330 (1985); Yip et al, *J. Phys. Chem.*, 95:6078–6081 (1991); and Zhu et al, *J. Photochem.*, 39:317–332 (1987)). The decay of the transient aci-nitro absorbance is commonly taken to be concomitant with cleavage of the caging group (McCray et al, *Ann. Rev. Biophys. Biophys. Chem.*, 18:239–270 (1989); and Walker et al, *J. Am. Chem. Soc.*, 110:7170–7177 (1988)).

More specifically, a 660 $\mu$M solution of the Nmoc-Glu was prepared in 150 mM NaCl, 10 mM phosphate buffer (pH 7.2). The stirred solution was photolyzed with 308 nm, 100 mJ, 10 ns pulsed emission from a XeCl excimer laser (Questek 2110) while the absorbance of the solution at 440 nm was measured. By monitoring the appearance and decay of the absorbance due to the aci-nitro intermediate generated by photolysis, the kinetics of uncaging could be examined (McCray et al, supra; and Walker et al, supra). In some runs, the experimental solution was continuously purged with nitrogen gas, although purging produced no observable difference in the kinetic behavior of the system. The results are shown in FIG. 6.

Figure 6:
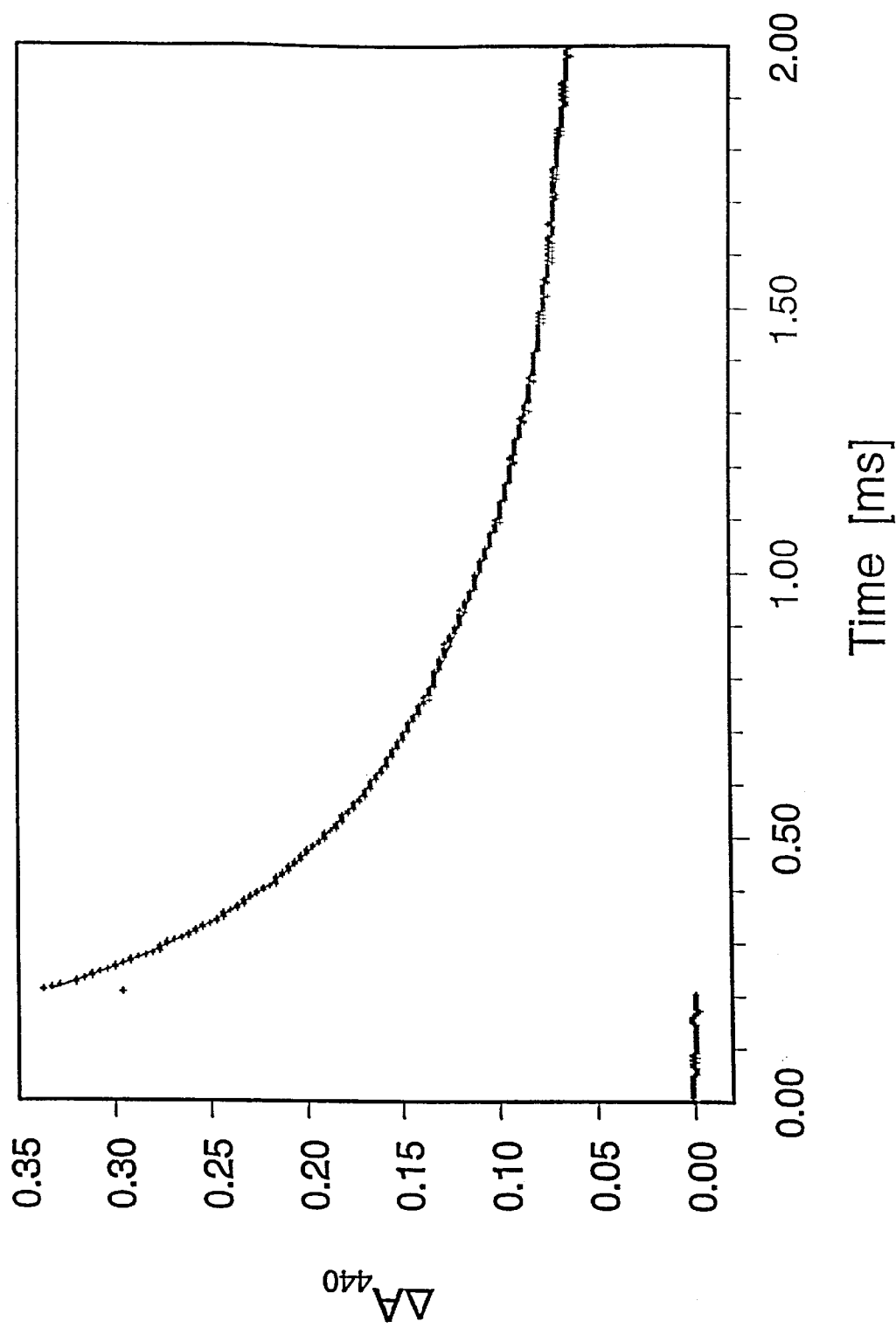
FIG. 6 shows transient absorbance changes following pulsed laser photolysis of Nmoc-Glu.

As shown in FIG. 6 the decay is dominated by a major component with a time constant (1/e) of 550±3 $\mu$s. A minor fast component contributes to the early part of the decay. The minor component has a time constant of 103±2 $\mu$s and accounts for ≦20% of the total decay amplitude. The major fast component, i.e., removal of the nitromandelyl moiety of the caging group, occurs with rate constant $k=1820$ s$^{-1}$ ($t_{1/2}=380$ $\mu$s). Analysis of multi-exponential decay data was preformed with KINFIT software (On-Line Instrument Systems, Inc., Boagrt, Ga.). Photolytic removal of the nitromandelyl group leaves the carbamate of glutamate (FIG. 3; Compound 8). Subsequent loss of $CO_2$ (decarboxylation) liberates free glutamate. The rate of decarboxylation to yield free glutamate could not be determined easily by spectroscopic means, but it could be estimated indirectly through electrophysiological measurements described in Example 2 below.

EXAMPLE 2

In vivo Photorelease of Glu

The quantum yield, $\phi$, represents the probability that an absorbed photon will lead to photorelease. The quantum yield, therefore, does not, in itself, allow one to estimate actual yield of glutamate photoreleased under physiological experimental conditions, which also depends on the extinction coefficient of the caged compound at the wavelength of irradiation, the concentration of the caged reagent used, and the incident light intensity. The most important empirical parameter is the duration of light exposure that is required to achieve a desired concentration of free glutamate. As a result, experiments were carried out to determine the minimal UV pulse duration that is required under typical experimental conditions.

More specifically, under conditions that optimized the activation of non-NMDA GluR channels relative to other ion channel types (i.e., tetrodotoxin and DL-2-amino-5-phosphonovaleric acid in the external solution, and Cs$^+$ in the internal pipet solution), an excised outside-out membrane patch (Hamill et al, *Pflügers Arch.*, 391:85–100 (1981)) was subjected to three 5 ms UV pulses using an argon ion laser, in the presence of cyclothiazide (100 $\mu$M) which blocks GluR desensitization (Yamada et al, *J. Neurosci.*, 13:3904–3915 (1993)), and a submaximal concentration of Nmoc-Glu (300 $\mu$M) at pH 6.3.

The argon ion laser (Coherent I90-5) configured to emit at 351–364 nm (400 mW). The output of the laser was gated by a laser shutter (Uniblitz LS2, Vincent Associates), controlled by the data acquisition software (pClamp, Axon Instruments). The shutter exhibits a delay to full opening of 1.5 ms—the composite result of an 800 $\mu$s induction delay and a 700 $\mu$s interval for complete movement of the shutter blade. The laser beam was steered into an inverted microscope (Diaphot, Nikon) through the epifluorescence port and was reflected by a 400 nm long-pass dichroic mirror through the back aperture of an oil-immersion objective (Fluor X40, N.A. 1.3, Nikon). A divergent fused silica lens (−150 mm focal length) was placed 20 cm in front of the dichroic mirror so that the laser beam was imaged onto a spot ~50 μm in diameter in the image plane. The light intensity at the sample is estimated at 70 μW/μm$^2$. Empirically, this intensity permitted a series of 5 ms light pulses to be delivered to the cells without any evidence of cell damage during electrophysiological recordings.

Figure 7:
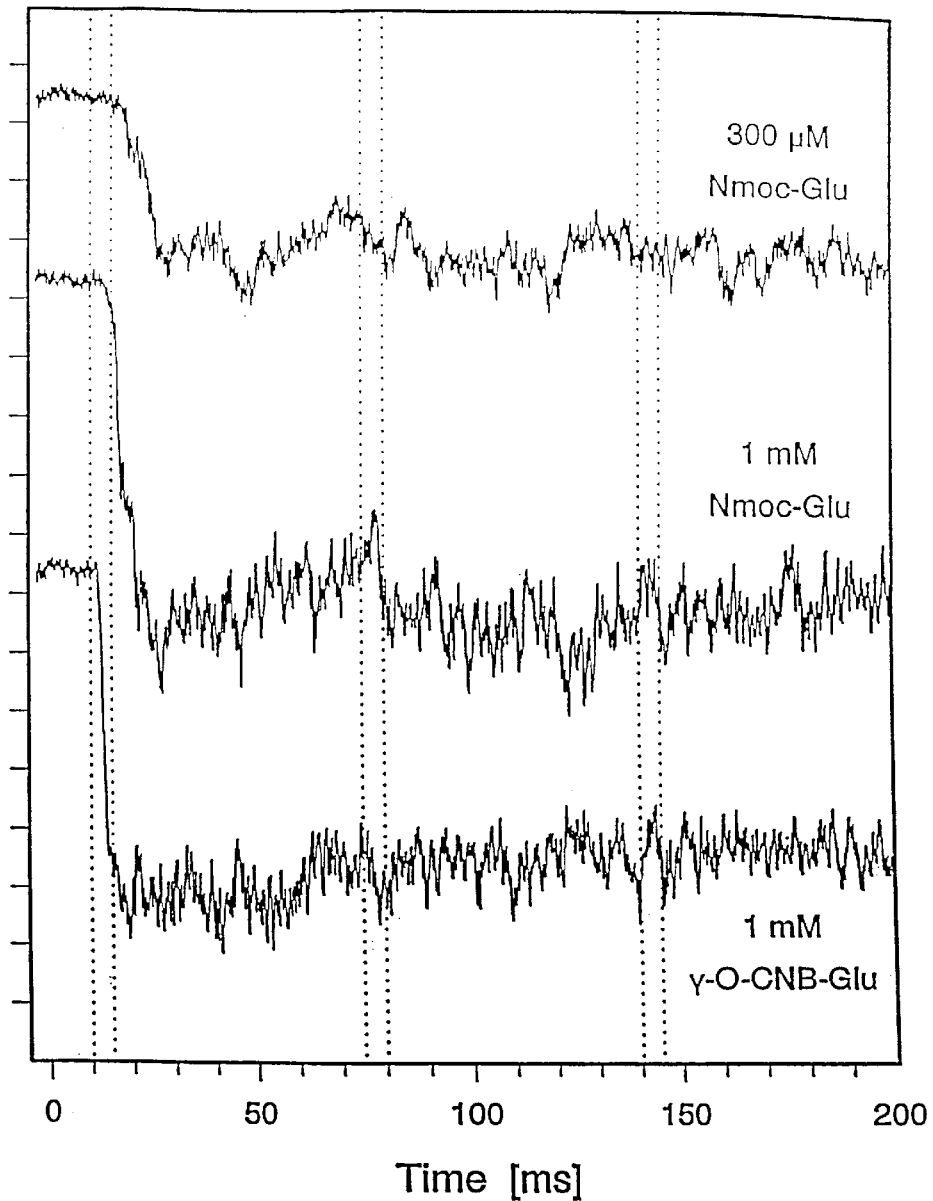
FIG. 7 shows the yield of photolysis of Nmoc-Glu achieved with 5 ms UV pulses.

The current response of the patch was determined under voltage clamp conditions using a patch clamp amplifier (Dagan 3900). The signals were filtered at 2 KHz, sampled at 5 KHz, and analyzed with pClamp software (Axon Instruments). The membrane potential was voltage clamped at −80 mV. The electrodes were placed in the same relative plane of focus as during the whole-cell recordings discussed below. Electrodes were pulled from borosilicate glass to a resistance of 10–40 MΩ. The extracellular solution was composed of 150 NaCl mM, 3.0 KCl mM, 2.0 mM CaCl$_2$, 1.0 mM MgCl$_2$, 10 mM N-(2-hydroxyethyl)piperazine-N'-(2-ethanesulfonic acid) (HEPES), adjusted to pH 7.3 with NaOH. For working at pH's below 7, piperazine-N,N'-bis (2-ethanesulfonic acid) (PIPES) was used as buffer instead of HEPES. Tetrodotoxin (TTX) (1.0 μM) and DL-2-amino-5-phosphonovaleric acid (APV) (100 μM) were added to the external solutions. The results are shown in FIG. 7.

If photolysis was incomplete after the first UV pulse, one would expect the current response to increase further after subsequent light flashes caused more uncaging. However, as shown in FIG. 7 (top trace), when the UV pulse duration was≦5 ms, flashes subsequent to the first caused no further increase in current response. The absence of further current increases after the first light pulse is consistent with complete photolysis following a single light pulse. To verify that the failure of the second and third UV flashes to produce increases in current response was not due to receptor saturation by photorelease from 300 μM Nmoc-Glu (FIG. 7, top trace), the experiment was repeated with 1.0 mM Nmoc-Glu (FIG. 7, middle trace). Increasing the Nmoc-Glu concentration increased the absolute amplitude of the current response, but not the relative magnitude of responses elicited by the three pulses. These results verified that the receptors were not saturated by photolysis of 300 μM Nmoc-Glu, and that photolysis was complete after a single 5 ms UV pulse.

One way to characterize the kinetics of glutamate release from Nmoc-Glu is through comparison with the behavior of γ-CNB-Glu, a caged glutamate known to exhibit fast photorelease kinetics (Wieboldt et al, supra (1994a)). As shown in FIG. 7, which compares the current responses of an excised outside-out membrane patch to glutamate photorelease from 1.0 mM Nmoc-Glu (middle trace) and from 1.0 mM γ-CNB-Glu (bottom trace), in the presence of 100 μM cyclothiazide to block desensitization, two differences between the compounds are apparent. First, the current induced by photorelease from Nmoc-Glu showed delayed onset and exhibited sigmoidal character. Second, the rate of rise of the inward current was moderately slower for Nmoc-Glu than for γ-CNB-Glu (10% to 90% rise time of 5.4 ms vs 1.9 ms, respectively). Because GluR desensitization was blocked by cyclothiazide in these experiments, the estimated rise times are indicative of the relative kinetics of photorelease from the two caged compounds, but may not represent absolute measures of the rates of photorelease. The delayed onset and the sigmoidal shape of the inward current response are consistent with the two-step uncaging process outlined in FIG. 3. The slower rate of rise of the current response to Nmoc-Glu photorelease is consistent with the rate-limiting decarboxylation step before release of free glutamate.

Next, a hippocampal neuron was dissociated from 20 day-old rat embryos, and plated onto 25 mm diameter No. 1 coverslip which had been acid-washed and coated with collagen, and maintained in culture for 2–3 weeks (Tang et al, Neuron, 13:1385–1393 (1994)). Then, whole-cell current response of the hippocampal neuron to a 5 ms photorelease from 10 mM Nmoc-Glu (pH 6.3) was determined under voltage clamp conditions using a patch clamp amplifier (Dagan 3900). Electrodes were pulled from borosilicate glass to a resistance of 3–5 MΩ. Series resistance of the electrode was compensated 80–90% during whole-cell recordings. The signals were filtered at 2 KHz, sampled at 5 KHz, and analyzed with pClamp software (Axon Instruments). The membrane potential was voltage clamped at −80 mV. To attenuate the peak current amplitude, the extracellular Na$^+$ concentration was reduced to 25 mM by closing the field diaphragm of the objective in order to achieve a sharply delimited spot of photolysis without decreasing light intensity, and photolysis was restricted to a 30 μm diameter spot over the soma. The reduction in Na$^+$ was compensated by replacement with choline. The 10% to 90% risetime was 0.98 ms. The results are shown in FIG. 8.

Figure 8:
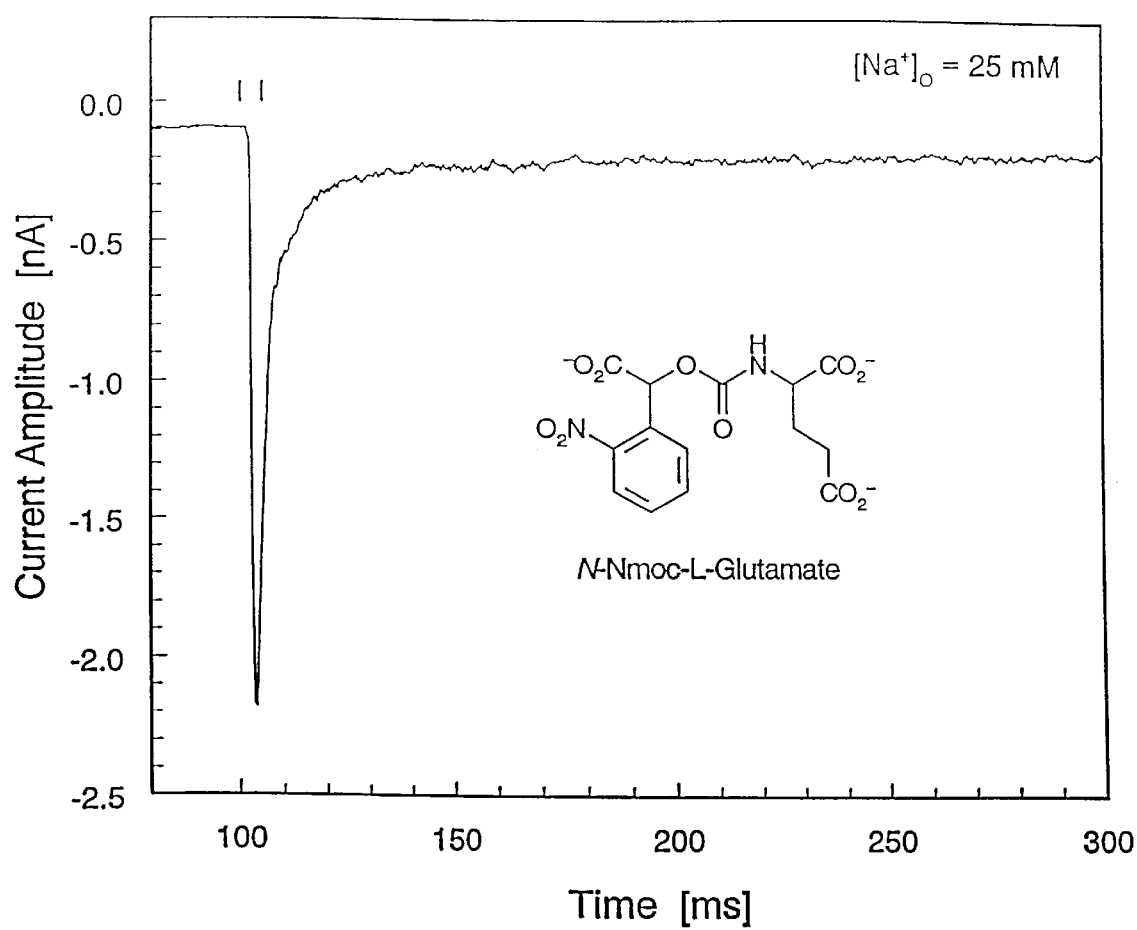
FIG. 8 shows changes in inward current in a hippocampal neuron due to the photorelease of Nmoc-Glu.

As shown in FIG. 8, photorelease of free glutamate from Nmoc-Glu evokes a robust inward current.

The results of previous studies suggest that the rate of decarboxylation to yield free glutamate should increase with decreased pH (Caplow, J. Am. Chem. Soc., 90:6795–6803 (1968); and Corrie et al, supra). As a result, physiological studies were carried out to confirm this prediction.

More specifically, whole-cell current response of a hippocampal neuron to 5 ms photolyses of 10 mM Nmoc-Glu at pH 6.2, 6.7, and 7.2, was carried out as described above. The results are shown in FIG. 9.

Figure 9:
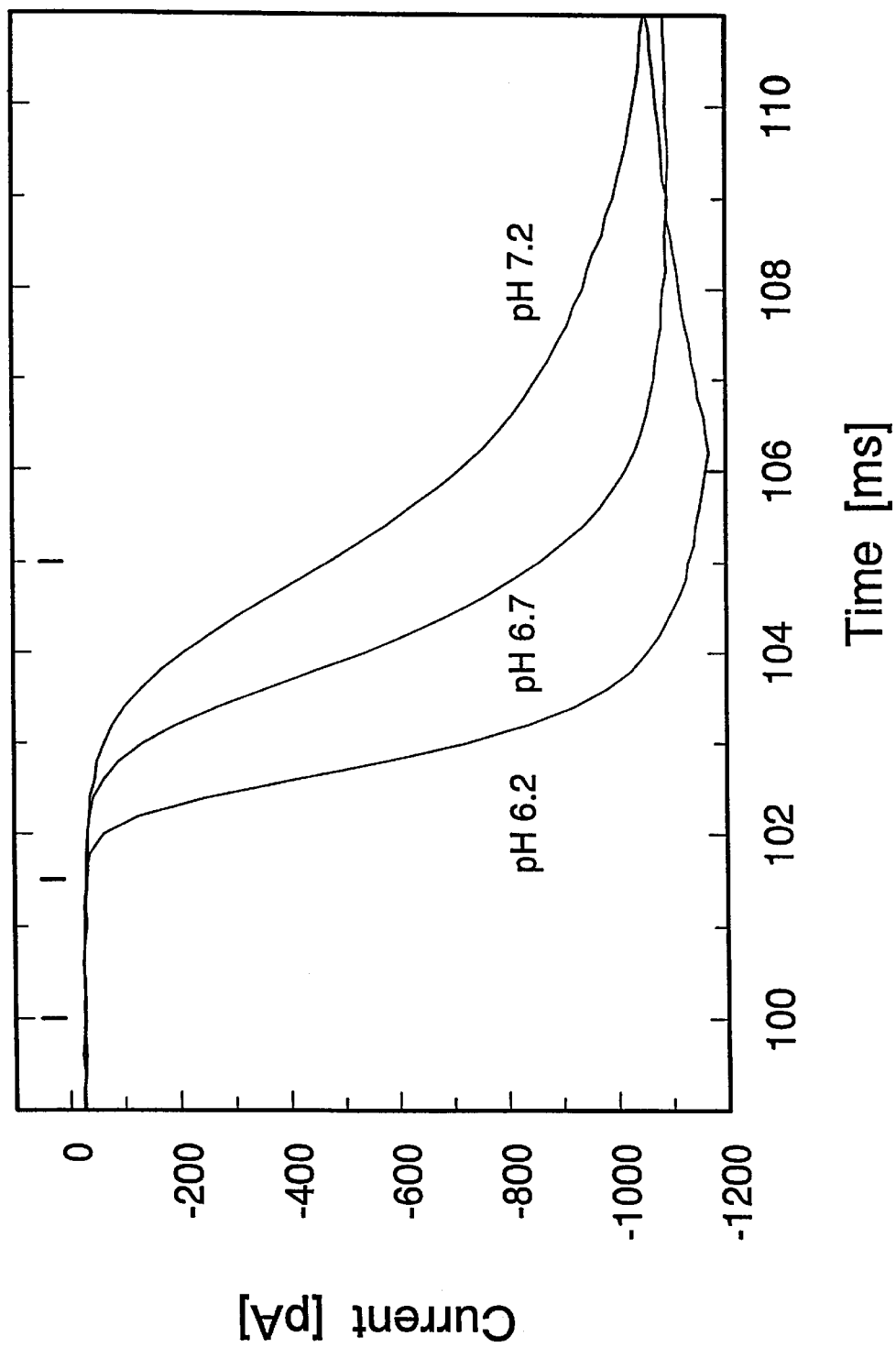
FIG. 9 shows pH-dependent photorelease of glutamate from Nmoc-Glu.

As shown in FIG. 9, the rate of current activation increases significantly with lowered pH, reflecting acceleration of the decarboxylation reaction. The 10% to 90% risetimes were 1.8, 3.0, and 4.8 ms, at pH 6.2, 6.7, and 7.2, respectively. These results suggest that glutamate photorelease from Nmoc-Glu is at least an order of magnitude faster than from NPEOC-Glu, another chemically stable caged glutamate (Corrie et al, supra).

Next, the pre-photolysis bioactivity and resistance to spontaneous hydrolysis of Nmoc-Glu were assessed by measuring whole-cell current responses to applications of Nmoc-Glu in the absence of light. For these experiments, 1.0 mM solutions of caged compounds were freshly prepared from solid samples, stored on ice in a dark container, and used within 30 min of preparation. Caged reagent solutions were delivered to each tested neuron via a light-protected solenoid-controlled perfusion pipette, in 10 μl aliquots. Each aliquot was sufficient to blanket the entire visible surface of the cell. As a control, γ-CNB-Glu was applied in an identical manner. The results are shown in FIG. 10A.

Figure 10A:
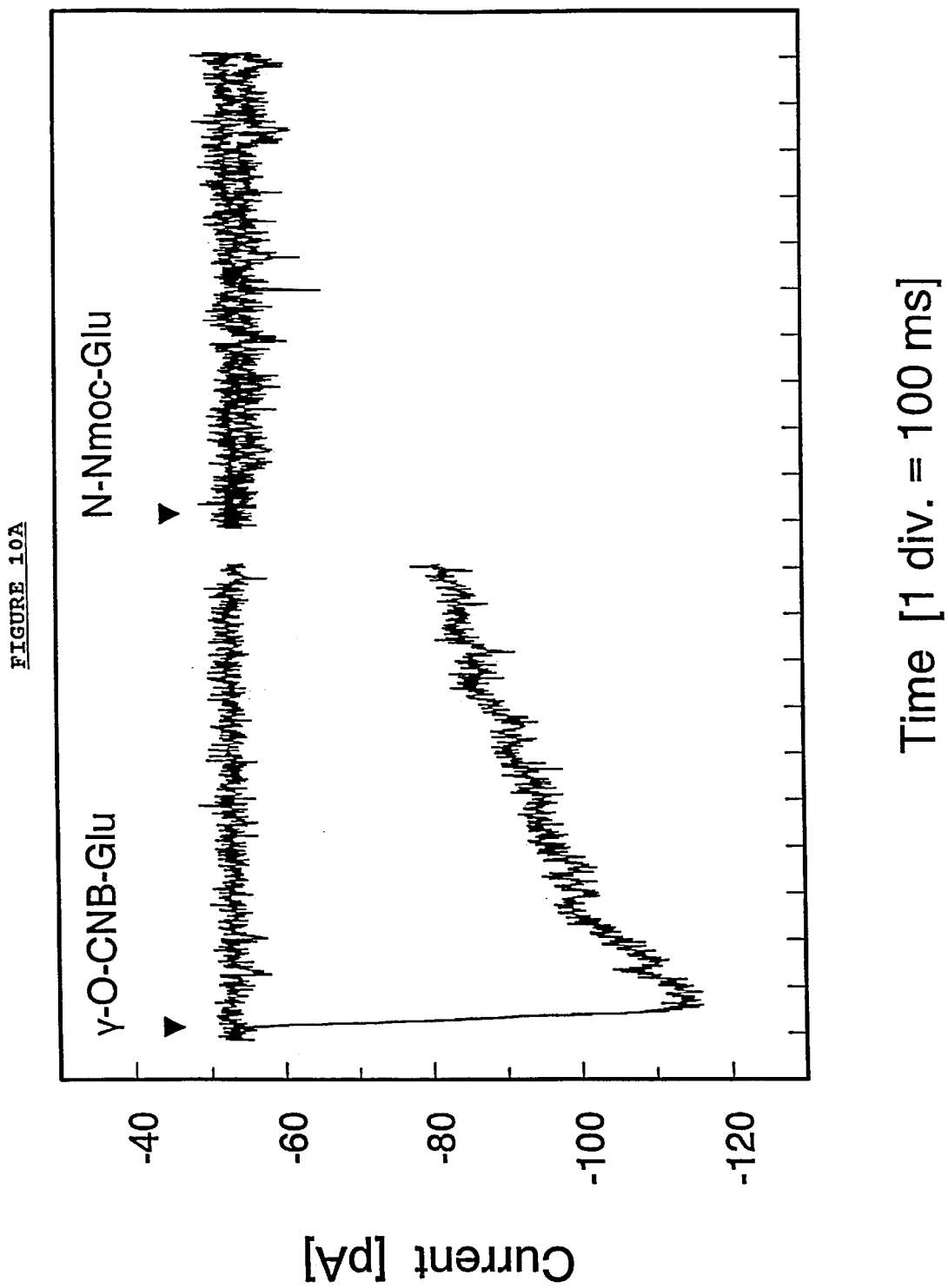
FIGS. 10A–10B show pre-photolysis activity of γ-O-CNB-Glu (FIG. 10A); and Nmoc-Glu (FIG. 10B).

As shown in FIG. 10A, in the absence of light, Nmoc-Glu was essentially inert, whereas γ-CNB-Glu still activated an inward current response. Using the same stock solutions, the comparison was repeated over a period of 2.5 hr. Thus, paired tests were performed as in the same manner on groups of 2–3 individual cells at various times after the reagent solutions had been at room temperature. The results are shown in FIG. 10B.

Figure 10B:
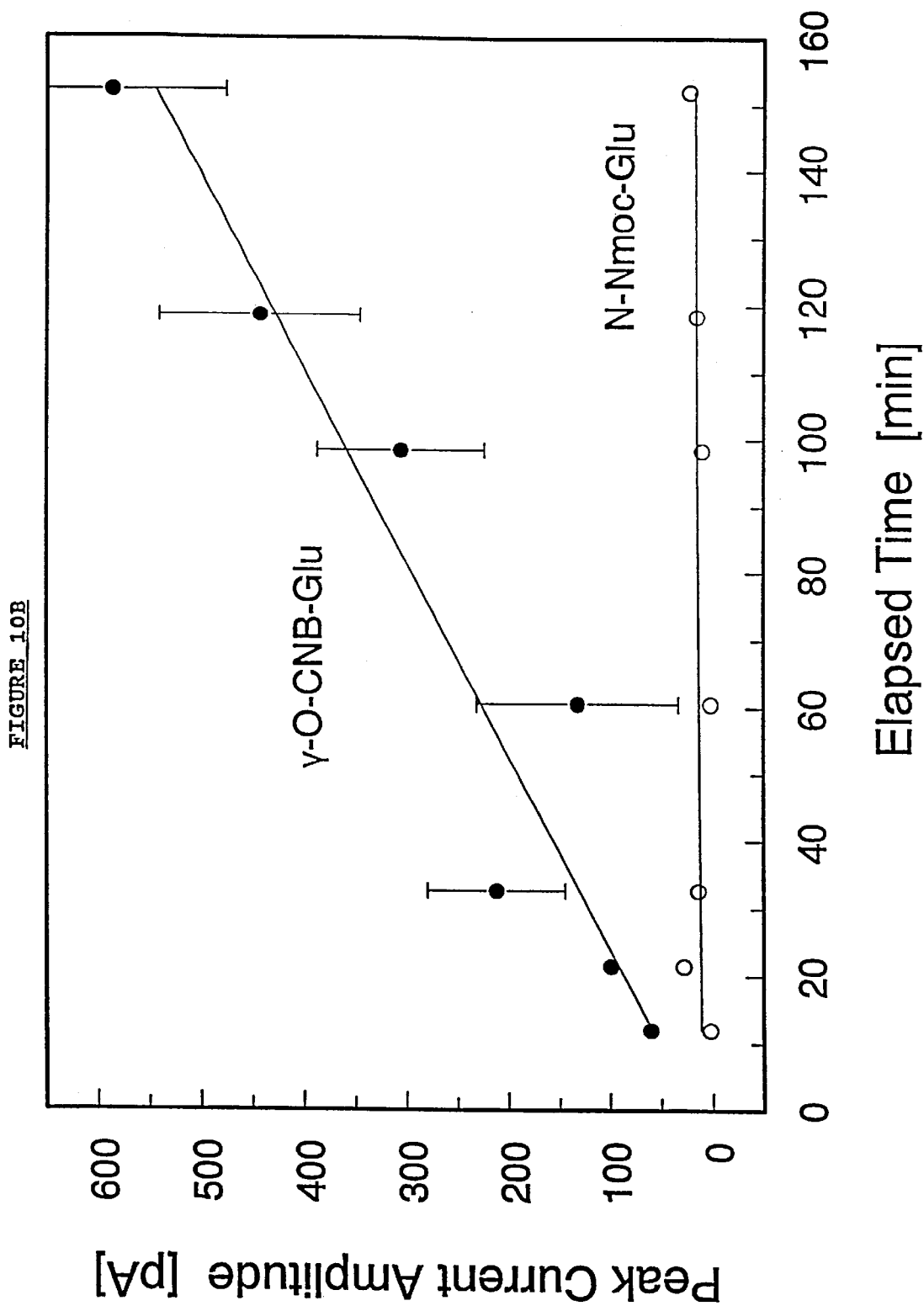

As shown in FIG. 10B, wherein pre-photolysis activity is expressed as the peak inward current evoked by direct application of caged reagent solution, whereas Nmoc-Glu remained biologically inert throughout, the pre-photolysis bioactivity of γ-CNB-Glu progressively increased with time.

While the invention has been described in detail, and with reference to specific embodiments thereof, it will be apparent to one of ordinary skill in the art that various changes and modifications can be made therein without departing from the spirit and scope thereof.

What is claimed:

1. A compound represented by structural Formulae (I), (II), (IV), (V), (VI) or (VII):

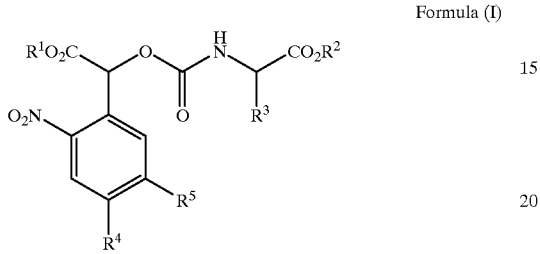

Formula (I)

wherein $R^1$ and $R^2$, which may be the same or different, are each selected from the group consisting of H, Li, Na, K, Cs, an alkyl group having from 1 to 5 carbon atoms, $NH_4$, and —$CH_2O_2C$—$R^{1a}$, wherein $R^{1a}$ is an alkyl group having from 1 to 5 carbon atoms; additionally $R^2$ is selected from the group consisting of 3,4-dihydro-4-oxo-1,2,3-benzotriazin-3-yl, 2-nitrophenyl, 4-nitrophenyl, pentachlorophenyl, pentafluorophenyl, and N-succinimidyl;

wherein $R^3$ is selected from the group consisting of H, an alkyl group having from 1 to 5 carbon atoms, $CH_3$—S—$(CH_2)_2$—, benzyl, and —$(CH_2)_n$—(CO)—Y, wherein n is an integer of from 1 to 5 and Y is $OR^{3a}$ or $NR^{3b}R^{3c}$, wherein $R^{3a}$, $R^{3b}$ and $R^{3c}$, which may be the same or different, are each selected from the group consisting of H and an alkyl group having from 1 to 5 carbon atoms, and $R^{3a}$ may additionally be selected from the group consisting of Li, Na, K and Cs;

wherein $R^4$ and $R^5$, which may be the same or different, are each selected from the group consisting of H, an alkyl group having from 1 to 5 carbon atoms, F, Cl, Br, CN, $NO_2$, $CO_2R^{4a}$, $OR^{4a}$, wherein $R^{4a}$ is selected from the group consisting of H, Li, Na, K, Cs, an alkyl group having from 1 to 5 carbon atoms, $NH_4$, and —$CH_2O_2$—$R^{4b}$, wherein $R^{4b}$ is an alkyl group having from 1 to 5 carbon atoms; and wherein optionally, $R^4$ and $R^5$ together from a methylenedioxy (O—$CH_2$—O) linkage;

Formula (II)

wherein $R^6$ is selected from the group consisting of H, t-utyloxycarbonyl (Boc), benzyloxycarbonyl (Cbz), 9-luorenylmethyloxycarbonyl (Fmoc), and a group represented by structural Formula (III);

wherein $R^7$ is selected from the group consisting of H, Li, Na, K, Cs, an alkyl group having from 1 to 5 carbon atoms, $NH_4$, 3,4-dihydro-4-oxo-1,2,3-benzotriazin-3-yl, 2-nitrophenyl, 4-nitrophenyl, pentachlorophenyl, pentafluorophenyl, and N-succinimidyl, and —$CH_2O_2C$—$R^{7a}$, wherein $R^{7a}$ is an alkyl group having from 1 to 5 carbon atoms;

wherein $R^8$ is selected from the group consisting of —$(CH_{2-p}(CH_3)_p)$—Y—$R^{8a}$, —$(CH_{2-p}(CH_3)_p)$—$C_6H_4$—Y—$R^{8a}$, wherein p is 0, 1, or 2, Y is O or S, wherein $R^{8a}$ is a group represented by structural Formula (III), and —$(CH_2)_q$—Z, wherein q is 3 or 4, and Z is —NH—$R^{8b}$ or —NH—C(=NH)—NH—$R^{8b}$, wherein $R^{8b}$ is a group represented by structural Formula (III);

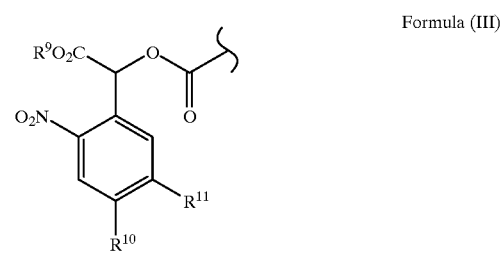

Formula (III)

wherein $R^9$ is selected from the group consisting of H, Li, Na, K, Cs, an alkyl group having from 1 to 5 carbon atoms, $NH_4$, and —$CH_2O_2C$—$R^{9a}$, wherein $R^{9a}$ is an alkyl group having from 1 to 5 carbon atoms;

wherein $R^{10}$ and $R^{11}$, which may be the same or different, are each selected from the group consisting of H, an alkyl group having 1 to 5 carbon atoms, F, Cl, Br, CN, $NO_2$, $CO_2R^{10a}$, and $OR^{10a}$, wherein $R^{10a}$ is selected from the group consisting of H, Li, Na, K, Cs, an alkyl group having from 1 to 5 carbon atoms, $NH_4$, and —$CH_2O_2C$—$R^{10b}$, wherein $R^{10b}$ is an alkyl group having from 1 to 5 carbon atoms; and wherein optionally, $R^{10}$ and $R^{11}$ together from a methylenedioxy (O—$CH_2$—O) linkage;

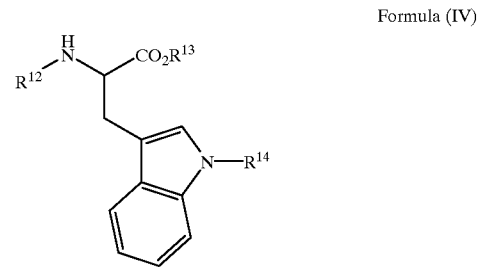

Formula (IV)

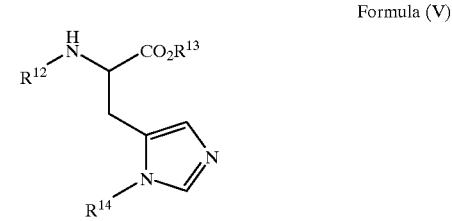

Formula (V)

Formula (VI)

Formula (VII)

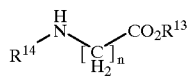

wherein $R^{12}$ is selected from the group consisting of H, t-butyloxycarbonyl (Boc), benzyloxycarbonyl (Cbz), 9-fluorenylmethyloxycarbonyl (Fmoc), and a group represented by structural Formula (III);

wherein $R^{13}$ is selected from the group consisting of H, Li, Na, K, Cs and an alkyl group having from 1 to 5 carbon atoms, $NH_4$, 3,4-dihydro-4-oxo-1,2,3-benzotriazin-3-yl, 2-nitrophenyl, 4-nitrophenyl, pentachlorophenyl, pentafluorophenyl, and N-succinimidyl, and —$CH_2O_2C$—$R^{13a}$, wherein $R^{13a}$, is an alkyl group having from 1 to 5 carbon atoms; and wherein $R^{14}$ is a group represented by structural Formula (III).

2. The compound of claim 1, wherein:

$R^1$ and $R^2$ are each selected from the group consisting of H, Na, K, methyl, ethyl, and t-butyl;

$R^3$ is selected from the group consisting of H, $CH_3$, —$CH(CH_3)_2$, —$CH_2$—$CH(CH_3)_2$, —$CH_2$—$CH(CH_3)$ ($CH_2CH_3$), —$CH_2CH_2SCH_3$, —$CH_2$—$C_6H_5$, —$CH_2CO_2H$, —$CH_2CONH_2$, —$CH_2CH_2CO_2H$, and —$CH_2CH_2CONH_2$;

$R^4$ and $R^5$ are each H or —$OCH_3$, or are combined together to form —$OCH_2O$—;

$R^6$ is selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc);

$R^7$ is selected from the group consisting of H, Na, K, methyl, ethyl, and t-butyl;

$R^8$ is selected from the group consisting of (t-butyl-o-nitromandelyloxycarbonyl)-$OCH_2$—, (t-butyl-o-nitromandelyloxycarbonyl)-$OCH(CH_3)$—, (t-butyl-o-nitromandelyloxycarbonyl)-$SCH_2$—, (t-butyl-o-nitromandelyloxycarbonyl)-$NH(CH_2)_4$—, (t-butyl-o-nitromandelyloxycarbonyl)-NH—C(=NH)—NH($CH_2)_3$—, and (t-butyl-o-nitromandelyloxycarbonyl)-O—$C_6H_4$—$CH_2$—;

$R^9$ is selected from the group consisting of H, $CH_3$, and t-butyl;

$R^{10}$ and $R^{11}$ are each H or —$OCH_3$, or are combined together to form —$OCH_2O$—;

$R^{12}$ is preferably selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc);

$R^{13}$ is selected from the group consisting of H, $CH_3$, and t-butyl; and $R^{14}$ is selected from the group t-butyl-o-nitromandelyloxycarbonyl (t-butyl Nmoc).

3. The compound of claim 1, wherein said compound is selected from the group consisting of N-(t-butyl Nmoc)-glycine, N-(t-butyl Nmoc)-L-alanine, N-(t-butyl Nmoc)-D-alanine, N-(t-butyl Nmoc)-L-valine, N-(t-butyl Nmoc)-D-valine, N-(t-butyl Nmoc)-L-leucine, N-(t-butyl Nmoc)-D-leucine, N-(t-butyl Nmoc)-L-isoleucine, N-(t-butyl Nmoc)-D-isoleucine, N-(t-butyl Nmoc)-L-methionine, N-(t-butyl Nmoc)-D-methionine, N-(t-butyl Nmoc)-L-phenylalanine, N-(t-butyl Nmoc)-D-phenylalanine, α-N-(t-butyl Nmoc)-L-aspartic acid, α-N-(t-butyl Nmoc)-D-aspartic acid, α-N-(t-butyl Nmoc)-L-asparagine, α-N-(t-butyl Nmoc)-D-asparagine, α-N-(t-butyl Nmoc)-L-glutamic acid, α-N-(t-butyl Nmoc)-D-glutamic acid, α-N-(t-butyl Nmoc)-L-glutamine, α-N-(t-butyl Nmoc)-D-glutamine, N-(t-butyl Nmoc)-L-proline, N-(t-butyl Nmoc)-D-proline, α-N-Fmoc-ε-N-(t-butyl Nmoc)-L-lysine, α-N-Fmoc-ε-N-(t-butyl Nmoc)-D-lysine, α-N-Fmoc-$N^G$-(t-butyl Nmoc)-L-arginine, α-N-Fmoc-$N^G$-(t-butyl Nmoc)-D-arginine, α-N-Fmoc-S-(t-butyl Nmoc)-L-cysteine, α-N-Fmoc-S-(t-butyl Nmoc)-D-cysteine, α-N-Fmoc-β-O-(t-butyl Nmoc)-L-serine, α-N-Fmoc-β-O-(t-butyl Nmoc)-D-serine, α-N-Fmoc-β-O-(t-butyl Nmoc)-L-threonine, α-N-Fmoc-β-O-(t-butyl Nmoc)-D-threonine, α-N-Fmoc-4-O-(t-butyl Nmoc)-L-tyrosine, α-N-Fmoc-4-O-(t-butyl Nmoc)-D-tyrosine, α-N-Fmoc-$N^{In}$-(t-butyl Nmoc)-L-tryptophan, α-N-Fmoc-$N^{In}$-(t-butyl Nmoc)-D-tryptophan, α-N-Fmoc-$N^{Im}$-(t-butyl Nmoc)-L-histidine, α-N-Fmoc-$N^{Im}$-(t-butyl Nmoc)-D-histidine, N-Nmoc-glycine, N-Nmoc-L-alanine, N-Nmoc-D-alanine, N-Nmoc-L-valine, N-Nmoc-D-valine, N-Nmoc-L-leucine, N-Nmoc-D-leucine, N-Nmoc-L-isoleucine, N-Nmoc-D-isoleucine, N-Nmoc-L-methionine, N-Nmoc-D-methionine, N-Nmoc-L-phenylalanine, N-Nmoc-D-phenylalanine, α-N-Nmoc-L-aspartic acid, α-N-Nmoc-D-aspartic acid, α-N-Nmoc-L-asparagine, α-N-Nmoc-D-asparagine, α-N-Nmoc-L-glutamic acid, α-N-Nmoc-D-glutamic acid, α-N-Nmoc-L-glutamine, α-N-Nmoc-D-glutamine, N-Nmoc-L-proline, N-Nmoc-D-proline, ε-N-Nmoc-L-lysine, ε-N-Nmoc-D-lysine, $N^G$-Nmoc-L-arginine, $N^G$-Nmoc-D-arginine, S-Nmoc-L-cysteine, S-Nmoc-D-cysteine, β-O-Nmoc-L-serine, β-O-Nmoc-D-serine, β-O-Nmoc-L-threonine, β-O-Nmoc-D-threonine, 4-O-Nmoc-L-tyrosine, 4-O-Nmoc-D-tyrosine, $N^{In}$-Nmoc-L-tryptophan, $N^{In}$-Nmoc-D-tryptophan, $N^{Im}$-Nmoc-L-histidine, $N^{Im}$-Nmoc-D-histidine, and N-Nmoc-4-aminobutyric acid.

4. The compound of claim 1, wherein said compound is present in an aqueous solution at a concentration of about $10^{-5}$ to $10^{-1}$ M.

5. The compound of claim 1, wherein said aqueous solution has a pH of about 6 to 8.

6. A method for producing a free amino acid or derivative thereof comprising the step of UV irradiating a compound represented by structural Formulae (I), (II), (IV), (V), (VI) or (VII):

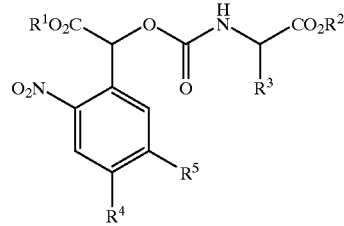

wherein $R^1$ and $R^2$, which may be the same or different, are each selected from the group consisting of H, Li, Na, K, Cs, an alkyl group having from 1 to 5 carbon atoms, $NH_4$, and —$CH_2O_2C$—$R^{1a}$, wherein $R^{1a}$ is an alkyl group having from 1 to 5 carbon atoms additionally, $R^2$ is selected from the group consisting of 3,4-dihydro-4-oxo-1,2,3-benzotriazin-3-yl, 2-nitrophenyl, 4-nitrophenyl, pentachlorophenyl, pentafluorophenyl, and N-succinimidyl;

wherein $R^3$ is selected from the group consisting of H, an alkyl group having from 1 to 5 carbon atoms, $CH_3$—

S—(CH$_2$)$_2$—, benzyl, and —(CH$_2$)$_n$—(CO)—Y, wherein n is an integer of from 1 to 5 and Y is OR$^{3a}$ or NR$^{3b}$R$^{3c}$, wherein R$^{3a}$, R$^{3b}$ and R$^{3c}$, which may be the same or different, are each selected from the group consisting of H and an alkyl group having from 1 to 5 carbon atoms, and R$^{3a}$ may additionally be selected from the group consisting of Li, Na, K and Cs;

wherein R$^4$ and R$^5$, which may be the same or different, are each selected from the group consisting of H, an alkyl group having from 1 to 5 carbon atoms, F, Cl, Br, CN, NO$_2$, CO$_2$R$^{4a}$, OR$^{4a}$, wherein R$^{4a}$ is selected from the group consisting of H, Li, Na, K, Cs, an alkyl group having from 1 to 5 carbon atoms, NH$_4$, and —CH$_2$O$_2$R$^{4b}$, wherein R$^{4b}$ is an alkyl group having from 1 to 5 carbon atoms; and wherein optionally, R$^4$ and R$^5$ together from a methylenedioxy (O—CH$_2$—O) linkage;

Formula (II)

wherein R$^6$ is selected from the group consisting of H, t-butyloxycarbonyl (Boc), benzyloxycarbonyl (Cbz), 9-fluorenylmethyloxycarbonyl (Fmoc), and a group represented by structural Formula (III);

wherein R$^7$ is selected from the group consisting of H, Li, Na, K, Cs, an alkyl group having from 1 to 5 carbon atoms, NH$_4$, 3,4-dihydro-4-oxo-1,2,3-benzotriazin-3-yl, 2-nitrophenyl, 4-nitrophenyl, pentachlorophenyl, pentafluorophenyl, and N-succinimidyl, and —CH$_2$O$_2$C—R$^{7a}$, wherein R$^{7a}$ is an alkyl group having from 1 to 5 carbon atoms;

wherein R$^8$ is selected from the group consisting of —(CH$_{2-p}$(CH$_3$)$_p$)—Y—R$^{8a}$, —(CH$_{2-p}$(CH$_3$)$_p$)—C$_6$H$_4$—Y—R$^{8a}$, wherein p is 0, 1, or 2, Y is O or S, wherein R$^{8a}$ is a group represented by structural Formula (III), and —(CH$_2$)$_q$—Z, wherein q is 3 or 4, and Z is —NH—R$^{8b}$ or —NH—C(=NH)—NH—R$^{8b}$, wherein R$^{8b}$ is a group represented by structural Formula (III);

Formula (III)

wherein R$^9$ is selected from the group consisting of H, Li, Na, K, Cs, an alkyl group having from 1 to 5 carbon atoms, NH$_4$, and —CH$_2$O$_2$C—R$^{9a}$, wherein R$^{9a}$ is an alkyl group having from 1 to 5 carbon atoms;

wherein R$^{10}$ and R$^{11}$, which may be the same or different, are each selected from the group consisting of H, an alkyl group having 1 to 5 carbon atoms, F, Cl, Br, CN, NO$_2$, CO$_2$R$^{10a}$, and OR$^{10a}$, wherein R$^{10a}$ is selected from the group consisting of H, Li, Na, K, Cs, an alkyl group having from 1 to 5 carbon atoms, NH$_4$, and —CH$_2$O$_2$C—R$^{10b}$, wherein R$^{10b}$ is an alkyl group having from 1 to 5 carbon atoms; and wherein optionally, R$^{10}$ and R$^{11}$ together from a methylenedioxy (O—CH$_2$—O) linkage;

Formula (V)

Formula (VI)

Formula (VII)

wherein R$^{12}$ is selected from the group consisting of H, t-butyloxycarbonyl (Boc), benzyloxycarbonyl (Cbz), 9-fluorenylmethyloxycarbonyl (Fmoc), and a group represented by structural Formula (III);

wherein R$^{13}$ is selected from the group consisting of H, Li, Na, K, Cs and an alkyl group having from 1 to 5 carbon atoms, NH$_4$, 3,4-dihydro-4-oxo-1,2,3-benzotriazin-3-yl, 2-nitrophenyl, 4-nitrophenyl, pentachlorophenyl, pentafluorophenyl, and N-succinimidyl, and —CH$_2$O$_2$C—R$^{13a}$, wherein R$^{13a}$ is an alkyl group having from 1 to 5 carbon atoms; and wherein R$^{14}$ is a group represented by structural Formula (III), and recovering said free amino acid or derivative thereof.

7. The method of claim 6, wherein:

R$^1$ and R$^2$ are each selected from the group consisting of H, Na, K, methyl, ethyl, and t-butyl;

R$^3$ is selected from the group consisting of H, CH$_3$, —CH(CH$_3$)$_2$, —CH$_2$—CH(CH$_3$)$_2$, —CH$_2$—CH(CH$_3$)(CH$_2$CH$_3$), —CH$_2$CH$_2$SCH$_3$, —CH$_2$—C$_6$H$_5$, —CH$_2$CO$_2$H, —CH$_2$CONH$_2$, —CH$_2$CH$_2$CO$_2$H, and —CH$_2$CH$_2$CONH$_2$;

R$^4$ and R$^5$ are each H or —OCH$_3$, or are combined together to form —OCH$_2$O—;

R$^6$ is selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc);

R$^7$ is selected from the group consisting of H, Na, K, methyl, ethyl, and t-butyl;

R⁸ is selected from the group consisting of (t-butyl-o-nitromandelyloxycarbonyl)-OCH$_2$—, (t-butyl-o-nitromandelyloxycarbonyl)-OCH(CH$_3$)—, (t-butyl-o-nitromandelyloxycarbonyl)-SCH$_2$—, (t-butyl-o-nitromandelyloxycarbonyl)-NH(CH$_2$)$_4$—, (t-butyl-o-nitromandelyloxycarbonyl)-NH—C(=NH)—NH(CH$_2$)$_3$—, and (t-butyl-o-nitromandelyloxycarbonyl)-O—C$_6$H$_4$—CH$_2$—;

R⁹ is selected from the group consisting of H, CH$_3$, and t-butyl;

R¹⁰ and R¹¹ are each H or —OCH$_3$, or are combined together to form —OCH$_2$O—;

R¹² is selected from the group consisting of 9-fluorenylmethyloxycarbonyl (Fmoc), t-butyloxycarbonyl (Boc), benzyloxycarbonyl (Cbz), and t-butyl-o-nitromandelyloxycarbonyl (t-butyl Nmoc);

R¹³ is selected from the group consisting of H, CH$_3$, and t-butyl; and

R¹⁴ is t-butyl-o-nitromandelyloxycarbonyl (t-butyl Nmoc).

8. The method of claim 6, wherein said compound is selected from the group consisting of N-(t-butyl Nmoc)-glycine, N-(t-butyl Nmoc)-L-alanine, N-(t-butyl Nmoc)-D-alanine, N-(t-butyl Nmoc)-L-valine, N-(t-butyl Nmoc)-D-valine, N-(t-butyl Nmoc)-L-leucine, N-(t-butyl Nmoc)-D-leucine, N-(t-butyl Nmoc)-L-isoleucine, N-(t-butyl Nmoc)-D-isoleucine, N-(t-butyl Nmoc)-L-methionine, N-(t-butyl Nmoc)-D-methionine, N-(t-butyl Nmoc)-L-phenylalanine, N-(t-butyl Nmoc)-D-phenylalanine, α-N-(t-butyl Nmoc)-L-aspartic acid, α-N-(t-butyl Nmoc)-D-aspartic acid, α-N-(t-butyl Nmoc)-L-asparagine, α-N-(t-butyl Nmoc)-D-asparagine, α-N-(t-butyl Nmoc)-L-glutamic acid, α-N-(t-butyl Nmoc)-D-glutamic acid, α-N-(t-butyl Nmoc)-L-glutamine, α-N-(t-butyl Nmoc)-D-glutamine, N-(t-butyl Nmoc)-L-proline, N-(t-butyl Nmoc)-D-proline, α-N-Fmoc-ε-N-(t-butyl Nmoc)-L-lysine, α-N-Fmoc-ε-N-(t-butyl Nmoc)-D-lysine, α-N-Fmoc-N$^G$-(t-butyl Nmoc)-L-arginine, α-N-Fmoc-N$^G$-(t-butyl Nmoc)-D-arginine, α-N-Fmoc-S-(t-butyl Nmoc)-L-cysteine, α-N-Fmoc-S-(t-butyl Nmoc)-D-cysteine, α-N-Fmoc-β-O-(t-butyl Nmoc)-L-serine, α-N-Fmoc-β-O-(t-butyl Nmoc)-D-serine, α-N-Fmoc-β-O-(t-butyl Nmoc)-D-threonine, α-N-Fmoc-β-O-(t-butyl Nmoc)-D-threonine, α-N-Fmoc-4-O-(t-butyl Nmoc)-L-tyrosine, α-N-Fmoc-4-O-(t-butyl Nmoc)-D-tyrosine, α-N-Fmoc-N$^{Im}$-(t-butyl Nmoc)-L-tryptophan, α-N-Fmoc-N$^{Im}$-(t-butyl Nmoc)-D-tryptophan, α-N-Fmoc-N$^{Im}$-(t-butyl Nmoc)-L-histidine, α-N-Fmoc-N$^{Im}$-(t-butyl Nmoc)-D-histidine, N-Nmoc-glycine, N-Nmoc-L-alanine, N-Nmoc-D-alanine, N-Nmoc-L-valine, N-Nmoc-D-valine, N-Nmoc-L-leucine, N-Nmoc-D-leucine, N-Nmoc-L-isoleucine, N-Nmoc-D-isoleucine, N-Nmoc-L-methionine, N-Nmoc-D-methionine, N-Nmoc-L-phenylalanine, N-Nmoc-D-phenylalanine, α-N-Nmoc-L-aspartic acid, α-N-Nmoc-D-aspartic acid, α-N-Nmoc-L-asparagine, α-N-Nmoc-D-asparagine, α-N-Nmoc-L-glutamic acid, α-N-Nmoc-D-glutamic acid, α-N-Nmoc-L-glutamine, α-N-Nmoc-D-glutamine, N-Nmoc-L-proline, N-Nmoc-D-proline, ε-N-Nmoc-L-lysine, ε-N-Nmoc-D-lysine, N$^G$-Nmoc-L-arginine, N$^G$-Nmoc-D-arginine, S-Nmoc-L-cysteine, S-Nmoc-D-cysteine, β-O-Nmoc-L-serine, β-O-Nmoc-D-serine, β-O-Nmoc-L-threonine, β-O-Nmoc-D-threonine, 4-O-Nmoc-L-tyrosine, 4-O-Nmoc-D-tyrosine, N$^{Im}$-Nmoc-L-tryptophan, N$^{Im}$-Nmoc-D-tryptophan, N$^{Im}$-Nmoc-L-histidine, N$^{Im}$-Nmoc-D-histidine, and N-Nmoc-4-aminobutyric acid.

9. The method of claim 6, wherein said irradiating is carried out at a wavelength of about 300 to 400 nm.

10. The method of claim 6, wherein said irradiating is carried out at about 10 to 40° C.

11. The method of claim 6, wherein said compound is present in an aqueous solution at a concentration of about $10^{-5}$ to $10^{-1}$ M.

12. The method of claim 11, wherein said aqueous solution has a pH of about 6 to 8.

13. The method of claim 6, wherein tissue or cultured cells are perfused with an aqueous solution comprising said compound and said tissue or cultured cells are subjected to said UV irradiation.

14. The method of claim 6, wherein a cell is microinjected with an aqueous solution comprising said compound and said cell is subjected to said UV irradiation.

* * * * *